(12) United States Patent
Harrison-Noonan et al.

(10) Patent No.: US 11,633,114 B2
(45) Date of Patent: Apr. 25, 2023

(54) CUFF DESIGNS AND METHODS

(71) Applicant: Apple Inc., Cupertino, CA (US)

(72) Inventors: Tobias J. Harrison-Noonan, San Francisco, CA (US); Richard H. Koch, Cupertino, CA (US); Habib S. Karaki, Sunnyvale, CA (US); Richard C. Kimoto, Fremont, CA (US); R. Keith Montgomery, Campbell, CA (US); Thomas J. Sullivan, San Jose, CA (US)

(*) Notice: Subject to any disclaimer, the term of this patent is extended or adjusted under 35 U.S.C. 154(b) by 392 days.

(21) Appl. No.: 15/578,624

(22) PCT Filed: Jun. 16, 2016

(86) PCT No.: PCT/US2016/037916
§ 371 (c)(1),
(2) Date: Nov. 30, 2017

(87) PCT Pub. No.: WO2016/205549
PCT Pub. Date: Dec. 22, 2016

(65) Prior Publication Data
US 2018/0153418 A1 Jun. 7, 2018

Related U.S. Application Data

(60) Provisional application No. 62/180,574, filed on Jun. 16, 2015.

(51) Int. Cl.
*A61B 5/022* (2006.01)
*A61B 5/0235* (2006.01)
*A61B 5/00* (2006.01)

(52) U.S. Cl.
CPC ...... *A61B 5/02233* (2013.01); *A61B 5/02225* (2013.01); *A61B 5/0235* (2013.01); *A61B 5/6824* (2013.01)

(58) Field of Classification Search
CPC ............... A61B 5/022; A61B 5/02233; A61B 5/02241; A61B 5/6831; A61B 5/02141;
(Continued)

(56) References Cited

U.S. PATENT DOCUMENTS 3,752,148 A * 8/1973 Schmalzbach ..... A61B 5/02233
600/499
3,978,848 A * 9/1976 Yen ..................... A61B 5/02208
600/494
(Continued)

FOREIGN PATENT DOCUMENTS

| EP | 1 671 580 A1 | 6/2006 |
| EP | 2 124 732 A2 | 12/2009 |
| EP | 2 823 758 A1 | 1/2015 |

OTHER PUBLICATIONS

Liz, Smith. "New AHA Recommendations for Blood Pressure Measurement: American Heart Association Practice Guidelines." Am Fam Physician 72.7 (2005): 1391-1398. (Year: 2005).*

*Primary Examiner* — David J. McCrosky
(74) *Attorney, Agent, or Firm* — Brownstein Hyatt Farber Schreck, LLP

(57) ABSTRACT

A low-profile blood pressure measurement system and methods of use are disclosed. The system includes an expandable member or structure that has a multi-compartment structure and/or is mounted on a rigid surface or structure. The system is incorporated into a portable multi-function device, or is configured to communicate with a portable multi-function device.

20 Claims, 20 Drawing Sheets

(58) Field of Classification Search
CPC .............. A61B 17/135; A61B 17/1355; A61H 9/0078; A61H 9/0092
See application file for complete search history.

(56) References Cited

U.S. PATENT DOCUMENTS

| | | | | |
|---|---|---|---|---|
| 4,469,107 | A * | 9/1984 | Asmar | A61B 5/02233 600/494 |
| 4,896,676 | A * | 1/1990 | Sasaki | A61B 5/02241 600/494 |
| 5,069,219 | A * | 12/1991 | Knoblich | A61B 5/02233 600/492 |
| 7,794,405 | B2 * | 9/2010 | Karo | A61B 5/02233 600/499 |
| 8,052,630 | B2 * | 11/2011 | Kloecker | A61F 5/34 601/151 |
| 8,114,026 | B2 * | 2/2012 | Leschinsky | A61B 5/02233 600/490 |
| 8,690,788 | B2 * | 4/2014 | Ide | A61B 5/02233 600/499 |
| 9,788,738 | B2 | 10/2017 | Barak et al. | |
| 2013/0046191 | A1 | 2/2013 | Lin et al. | |
| 2013/0053708 | A1 | 2/2013 | Quinn et al. | |
| 2015/0025399 | A1 * | 1/2015 | Nishibayashi | A61B 5/02233 600/492 |

\* cited by examiner

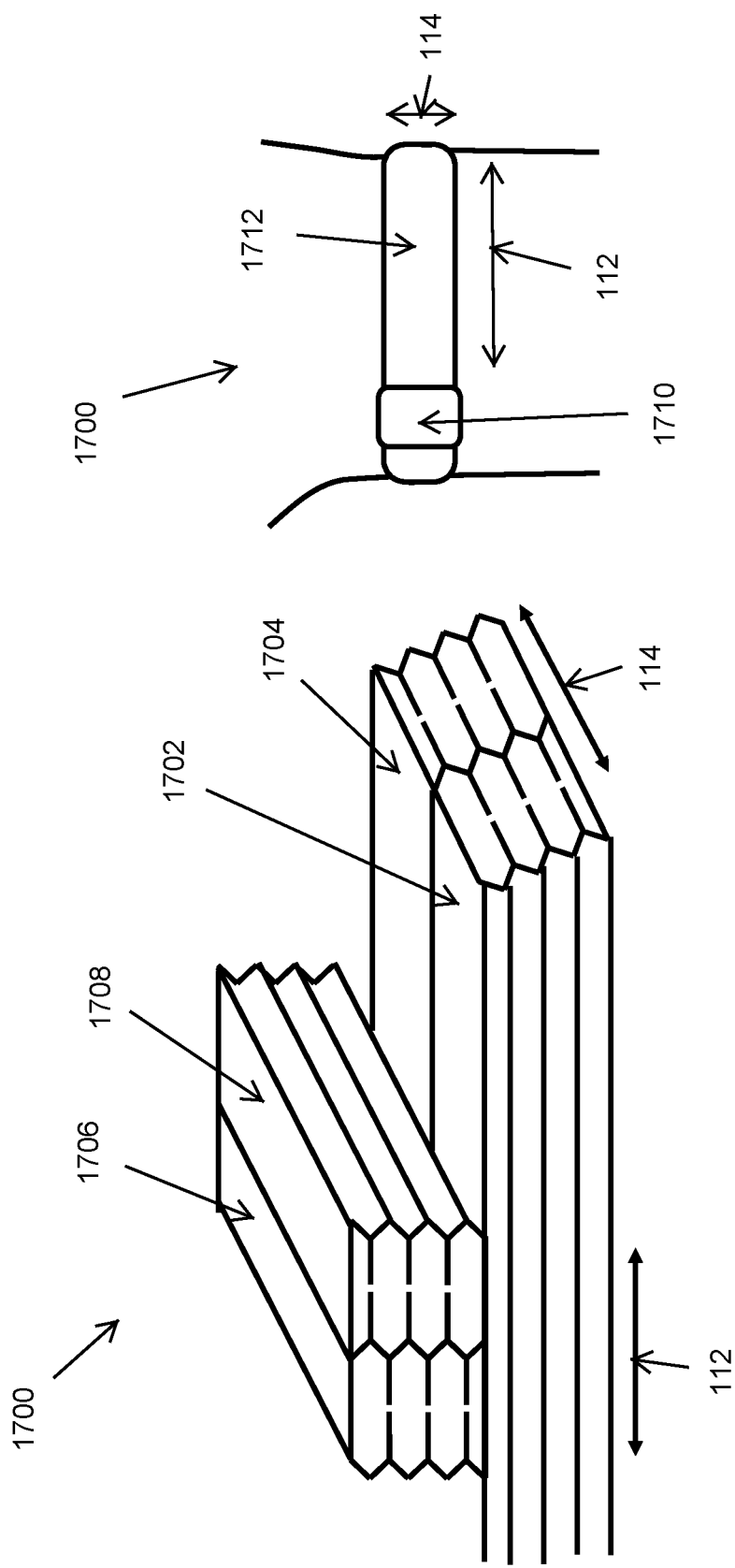

CUFF DESIGNS AND METHODS

CROSS-REFERENCE TO RELATED APPLICATIONS

This application is a National Phase Patent Application under 35 U.S.C. § 371 of International Application No. PCT/US2016/037916, filed Jun. 16, 2016, and claims the benefit of U.S. Provisional Application No. 62/180,574, filed on Jun. 16, 2015, which is hereby incorporated by reference in its entirety.

BACKGROUND

High blood pressure or hypertension is common medical condition, yet it often goes undetected or untreated. According to the Centers for Disease Control, 1 in 3 adult Americans have hypertension, and only about half of those diagnosed with the disease are under adequate blood pressure control.

Evidence-based guidelines for the management of high blood pressure are periodically updated by the Joint National Committee (JNC). In their 2014 guidelines, the JNC recommended the initiation of hypertension in patients 60 years and over, with a systolic blood pressure (SBP)≥150 mm Hg or a diastolic blood pressure (DBP)≥90 mm Hg, while in population under 60 years of age, or patients 18 years or older with chronic kidney disease or diabetes, treatment should be initiated in those with SBP≥140 mm Hg or DBP≥90 mm Hg.

The actual measurement of blood pressure can vary with a number of factors, including recent activity, body position at the time of measurement, ingested substances such as alcohol and caffeine, and current stress levels. Even the presence of a patient at a doctor's office can transiently increase blood pressure, a phenomenon known as "white coat hypertension". To obtain a more reliable and/or accurate assessment of a patient's blood pressure, a patient may be asked to periodically check and record their blood pressure at home, or to even wear an ambulatory blood pressure monitoring (ABPM) device for a period of time, typically a single 24-hour period. The ABPM device is often programmed or configured to inflate at intervals, e.g. every 15-20 minutes during the day, and every 20-30 minutes at night).

Blood pressure measurements may be performed in number of ways. In the ausculatory method, a pressure cuff is placed around the arm and is inflated sufficiently to occlude the brachial artery. The pressure is then decreased gradually and a stethoscope is used to detect Korotkoff sounds. The Korotkoff sounds are the result of turbulent flow through a partially occluded artery, and the pressures corresponding to the onset and cessation of the Korotkoff sounds are the systolic and diastolic blood pressures, respectively. In the oscillometric method, the onset and cessation of pulsatile pressure changes sensed in the cuff to determine the systolic and diastolic blood pressure. In the applanation tonometry method, a pressure sensor is placed against an artery to slightly flatten the artery against the underlying anatomical structures, so the pressure waveform can be directly measured. The central venous pressure, and the systolic and diastolic pressures can then be determined from the waveform.

BRIEF SUMMARY

A low-profile blood pressure measurement system and methods of use are disclosed. The system includes an expandable member that has a multi-compartment structure and/or is mounted on a rigid surface or structure. The system may be incorporated into a portable electronic device, or may be configured for use with, or to otherwise communicate with a portable multi-function device.

In one embodiment, a blood pressure measurement system is provided where the system comprises a pressure sensor, an expandable member or structure comprising a plurality of expandable cells, wherein the plurality of expandable cells comprises at least three expandable cells or at least two repeating expandable cells, and an expansion actuator configured to selectively expand the expandable member. The expandable member may be an inflatable structure, and the expandable cells may be inflatable cells and the expansion actuator may be an air pump. The expandable member may comprise a length, a width and a vertical dimension, and wherein the length is orthogonal to the width and the height and the width is orthogonal to the vertical dimension, and wherein the length is greater than equal to the width, and the width is greater than or equal to the vertical dimension. In some variations, the expandable member comprises a width in the range of about 10 mm to 40 mm, or about 20 mm to 30 mm. The expandable member may comprise a length in the range of about 100 mm to 400 mm, about 200 mm to 300 mm, or about 225 mm to 275 mm. In some examples, the expandable cells, when in an expanded state, may each comprise a generally rectangular structure comprising a length, a width that is smaller than the length and orthogonal to the length, and a vertical dimension that is orthogonal to the length and the width and smaller than the width. The plurality of expandable cells may comprise a stack of expandable cells, stacked along their vertical dimensions. Also, at least one opening may be provided in a wall between adjacent expandable cells, and the some variations, the opening may have a vertical opening axis. The expandable cells may comprise a variety of configurations and/or orientations. In some examples, the expandable cells, in an expanded state, may comprise a plurality of elongate structures, each structure comprising a length, width and vertical dimension. The plurality of expandable cells may comprise a side-by-side arrangement across their widths. The lengths of the plurality of expandable cells may be aligned with the length of the expandable member. The lengths of the plurality of expandable cells may be aligned with the width of the expandable member. The plurality of elongate cells may comprise an elongate cylindrical shape, an elongate oblong shape, a hexagonal cross-sectional shape transverse to their length, or an elongate teardrop shape, the elongate teardrop shape comprising an enlarged end and an tapered end, for example. In embodiments with teardrop shapes, the plurality of elongate teardrop shapes may be arranged along the vertical dimension of the expandable member in an alternating orientation, or may each have the same orientation along a length or a width of the expandable member. The expandable member may also further comprise an expandable sensing cell located on a skin contact surface of the expandable member. In some examples, the expandable cells may comprise a plurality of structures in a matrix configuration, with at least two expandable cells along the width of the expandable member, and at least two expandable cells along the vertical dimension of the expandable member. In other examples, the matrix configuration may comprise at least three expandable cells along the width of the expandable member and at least ten expandable cells along the length of the expandable member, or comprise at least two elongate hexagonal structures along the vertical dimension of the expandable member, and at least three elongate hexagonal structure along the width dimension of the expandable member. Sometimes, the expandable member may further comprise wall openings between adjacent elongate hexagonal structures. In some variations, the adjacent elongate hexagonal structures may be vertically aligned, and/or horizontally adjacent. The expandable cells each comprise a superior surface, an inferior surface, and a lateral surface between the superior and inferior surfaces. In some variations, the lateral surface of the each expandable cell may be folded outward or inward when in a collapsed state. In some examples, the expandable member may be characterized or otherwise further comprise a first plurality of elongate expandable cells and a second plurality of elongate expandable cells, wherein the first plurality of elongate expandable cells comprises lengths that are aligned with the length of the expandable member, and wherein the second plurality of elongate expandable cells comprises length that are aligned with the width of the expandable member. In other examples, the expandable member may further comprise a first plurality of elongate expandable cells comprising lengths and a second plurality of elongate expandable cells comprising lengths, wherein the lengths of the first and second pluralities of elongate expandable cells have orthogonal orientations relative to the other. The system may also further comprise a frame member, the frame member comprising a rigid base, and wherein the expandable member is attached to the rigid base. The frame member may optionally further comprise a first side wall, a second side wall, and a cavity therebetween, wherein the expandable member is at least partially located in the cavity. In some instances, the expandable member may be configured to expand out of the cavity when in the expanded state. In some other embodiments, the inflatable structure may comprise a first expandable cell, a second expandable cell, and a third expandable cell therebetween, wherein the expansion actuator is configured to inflate the first and second expandable cells to a greater pressure than the third expandable cell. The first expandable cell is a first expandable edge cell and the second expandable cell is a second expandable edge cell. The expandable member may further comprise a sensing cell overlying the plurality of elongate structures.

BRIEF DESCRIPTION OF THE DRAWINGS

FIG. 17A is a schematic perspective view of an expandable member comprising a lower plurality of expandable cells and an upper plurality of expandable cells with different orientation than the lower plurality. FIG. 17B depicts the overall orientation of the expandable member in FIG. 17A with respect to the band of the blood pressure measurement system.

DETAILED DESCRIPTION

Blood pressure systems or kits are often configured with inflatable cuffs that are designed for detecting changes in pressure at either the upper arm via the brachial artery, or at the wrist via the radial artery. Cuffs are typically configured to accurately measure blood pressures in a limited range of limb sizes, and limbs that fall under or above the intended limb size may underestimate or overestimate the actual blood pressure, respectively. The cuffs of such systems are configured to have a width that is about 40% of the intended arm circumference and a length of about 80% the intended arm circumference. The air bladders of cuffs intended for average upper arm sizes have a width of about 5 cm or greater, and lengths of about 25 cm or more. Smaller cuffs may have difficulty sensing the pressure signals due to placement variations and the smaller contact surface area of the cuff.

Described herein are exemplary low-profile blood pressure measurement devices, comprising multiple compartments or cells. One or more expandable structures may be provided on a wearable device, coupled to or provided as an armband, wristband, or legband, for example. The wearable device may include a band and/or a housing. The band or housing may or may not include one or more of the following components: a visual display, speaker, power source, communication module, and an actuator for the expandable structure, such as a fluid pump. In other variations, one or more of these components may be provided in a separate secondary device, housing or structure from the primary wearable device, such as a portable electronic or multifunction device, such as a tablet, cellphone, watch or other wearable component. The separate secondary device may be coupled by a conduit, cable or tube to the expandable structure. In further variations, using the communication module, the device may be used in conjunction with a portable electronic or multifunction device, such as a tablet, cellphone or watch.

Figure 1A:
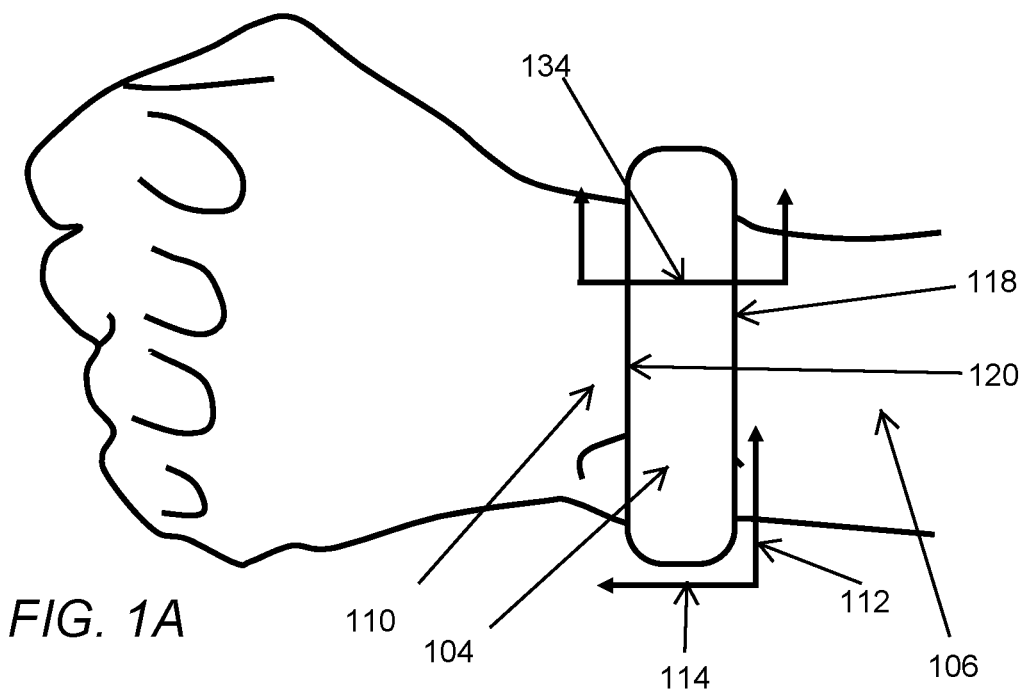
FIGS. 1A and 1B are posterior and anterior views of an exemplary blood pressure measurement system worn on the wrist.
Figure 1B:
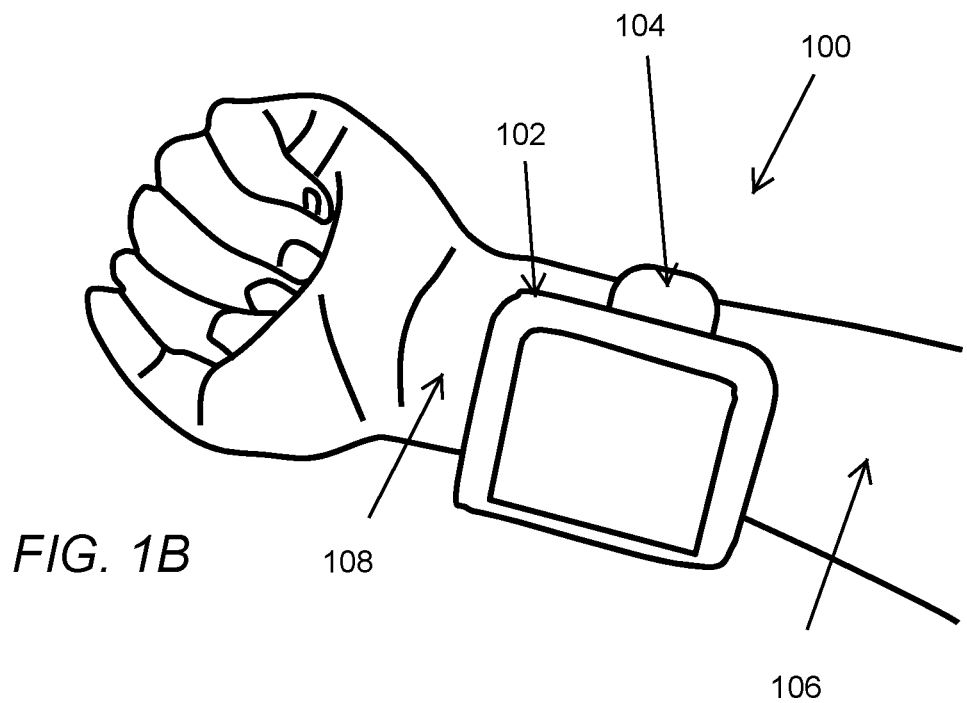

One example of a system for monitoring blood pressure is depicted in FIGS. 1A and 1B. The system 100 comprises a housing 102 and adjustable band 104 configured to attach the system 100 to the limb 106 of the user. An inflatable or expandable member which is configured to releasably apply pressure to the limb 106 may be incorporated into the housing 102 and/or band 104, and is described in greater detail below. In the particular example in FIGS. 1A and 1B, the system 100 is configured to be worn on the wrist, but in system may also be configured to be used at more proximal locations of the arm, or in the upper or lower leg. The system 100 in FIGS. 1A and 1B is depicted with the housing 102 located on the palmar or anterior surface 108 of the limb 106, and with the band 104 primarily located on the dorsal or posterior surface 110 of the limb 106, but this orientation may or may not be required. In other variations, the device may be configured without any housing, or may be used in the orientation depicted in FIGS. 1A and 1B, or in the opposite orientation, with the housing on the posterior surface 110 and the band 104 primarily on the anterior 108 surface. Also, the system 100 is depicted as being located on a left limb 106 of a user, but the device may also be configured or is configurable for use with the right limb.

Figure 2A:
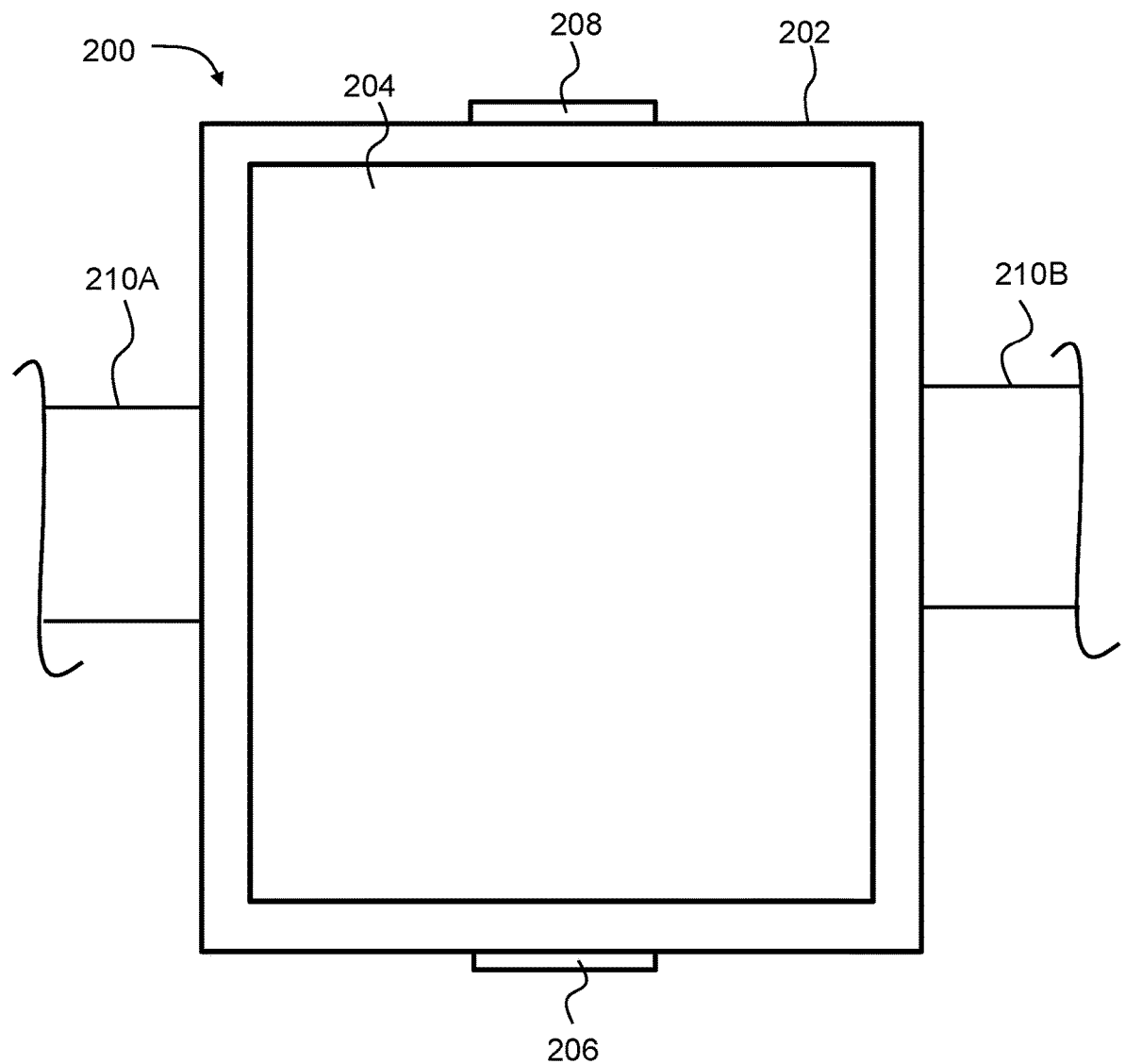
FIG. 2A illustrates a system in accordance with some embodiments.

FIG. 2A, illustrates exemplary device 200. Device 200 includes body 202. In some embodiments, device 200 has display screen 204 which may or may not be a touchscreen. The touch screen, touch surface, or other user input mechanism may or may not be force or intensity-sensitive. Alternatively, or in addition to screen 204, device 200 may have input mechanisms 206 and 208, if included, can be physical. Examples of physical input mechanisms include push buttons and rotatable mechanisms. In some embodiments, device 200 has one or more straps or bands 510a and 510b, which are configured to attach the device 200 to a limb.

Figure 2B:
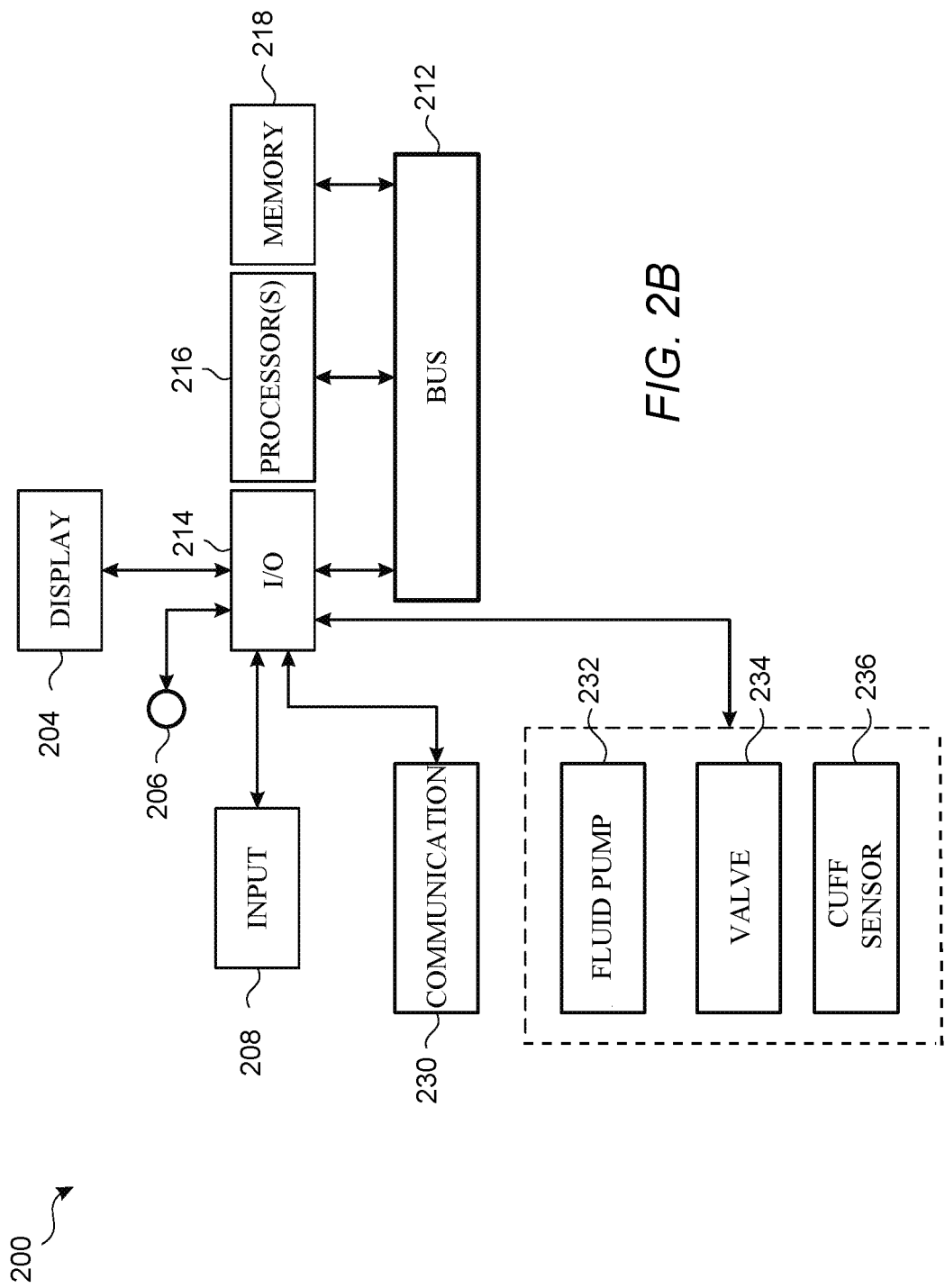
FIG. 2B is a block diagram illustrating an exemplary system.

FIG. 2B depicts the basic hardware architecture of exemplary device 200. Device 200 may include a bus 212 that operatively couples I/O section 214 with one or more computer processors 216 and memory 218. I/O section 214 can be connected to display 204, which optionally includes a touch-sensitive component and/or a touch-intensity sensitive component. In addition, I/O section 214 can be connected with communication unit 230 for receiving application and operating system data, using Wi-Fi, Bluetooth, near field communication (NFC), cellular, and/or other wireless communication techniques, and the like. Device 200 can include input mechanisms 206 and/or 208. Input mechanism 206 may be a rotatable input device and/or a depressible input device, for example. Input mechanism 208 may be the same or different type of input mechanism compared to input mechanism 206, in some examples.

Input mechanism 208 may be a microphone, in some examples. Device 200 can include various sensors or controllable components. In some embodiments, these will include a fluid or air pump 232, a bleed valve 234 and/or a cuff or pressure sensor 236. In other variations, the sensor may be a sound sensor, an optical sensor, including a photoplethysmography sensor, for example, or an electrical sensor. The sensor may comprise one or multiple sensor elements.

The pump 232 may be any of a variety of pumps configured to move and pressurize a liquid or gas. In some variations, the pump may comprise a diaphragm pump, including a piezoelectric microdiaphragm pump, a rotary pump, a helical pump, or a volumetric pump, such as a syringe pump. The pump may or may not be backdrivable. In some further variations, the pump may include a fluid reservoir, and the pump may be configured to pressurize the expandable member and may optionally be configured to also actively deflate the expandable member.

The bleed valve 234 may be any of a variety of valves, depending upon the desired complexity and the controller configuration. In some variations, the valve is normally biased closed but in other variation typically normally biased open. The valve may be an active valve that is mechanically or electrical actuated, such as a solenoid valve or voice coil valve, such that the controller can open or close, or control the resist or flow through the valve, e.g. the bleed rate of the expandable member when detecting blood pressure information, such as the pressure signal or waveform, and/or the onset and cessation of pressure oscillations or Korotkoff sounds, for example. In other variations, the valve may be a passive valve that is not actively controlled by the device, but is mechanically configured with a bleed rate profile that permits the device to build up a pressure in the expandable member where the pump configured to exceed the bleed rate of the valve, but the cuff pressure may only be controlled via the flow rate of the pump because of the persistent bleed or leak from the valve. Although pump 232 and valve 234 are schematically depicted as distinct mechanisms in FIG. 2B, in some variations, the pump 232 and valve 234 may be integrally formed. It some further variations, a valve mechanism may not be required based upon the system design or pump functionality. For example, in some variations, a pump may resist air or fluid flow when the pump is in the "off" state, but may permit flow or otherwise generates flow when in the "on" state. Likewise, some pumps, such as certain diaphragm pumps, may be in open in the "off" state to permit flow in one or both directions, but may resist flow in at least one direction when the pump is in the "on" state and generating flow.

The device 200 further comprises one or more pressure sensors in communication with at least a portion of the expandable member. The pressure sensor includes any of a variety of sensor configurations, including but not limited to mechanical strain gauges, piezoelectric and MEMS sensors. The device may also further comprise other sensors, including but not limited to a temperature sensor. In some variations, the temperature sensor may be used to calibrate or correct for temperature variations in the pressure sensor, but other variations may comprise temperature correcting bridge circuits, such as a Wheatstone bridge. The sensor may be configured for an oscillometry-based system or a tonometry-based system, an auscultatory-based system, or other type of blood pressure measurement system, for example. In some variations, a single pressure sensor may be provided, but in other variations, two or more pressure sensors may be provided. Each pressure sensor may be located coupled to a housing or a band. Sensors located on a band may be positioned directly on the band or an expandable member of the band. In some further variations, expandable members with a sensor may be characterized as sensing expandable members, and expandable members without a sensor may be characterized as actuating expandable members.

Memory 218 of device 200 can be a non-transitory computer-readable storage medium, for storing computer-executable instructions, which, when executed by one or more computer processors 216, for example, can cause the computer processors to perform the techniques described above. The computer-executable instructions can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. For purposes of this document, a "non-transitory computer-readable storage medium" can be any medium that can tangibly contain or store computer-executable instructions for use by or in connection with the instruction execution system, apparatus, or device. Device 200 is not limited to the components and configuration of FIG. 2B, but can include other or additional components in multiple configurations.

Figure 3A:
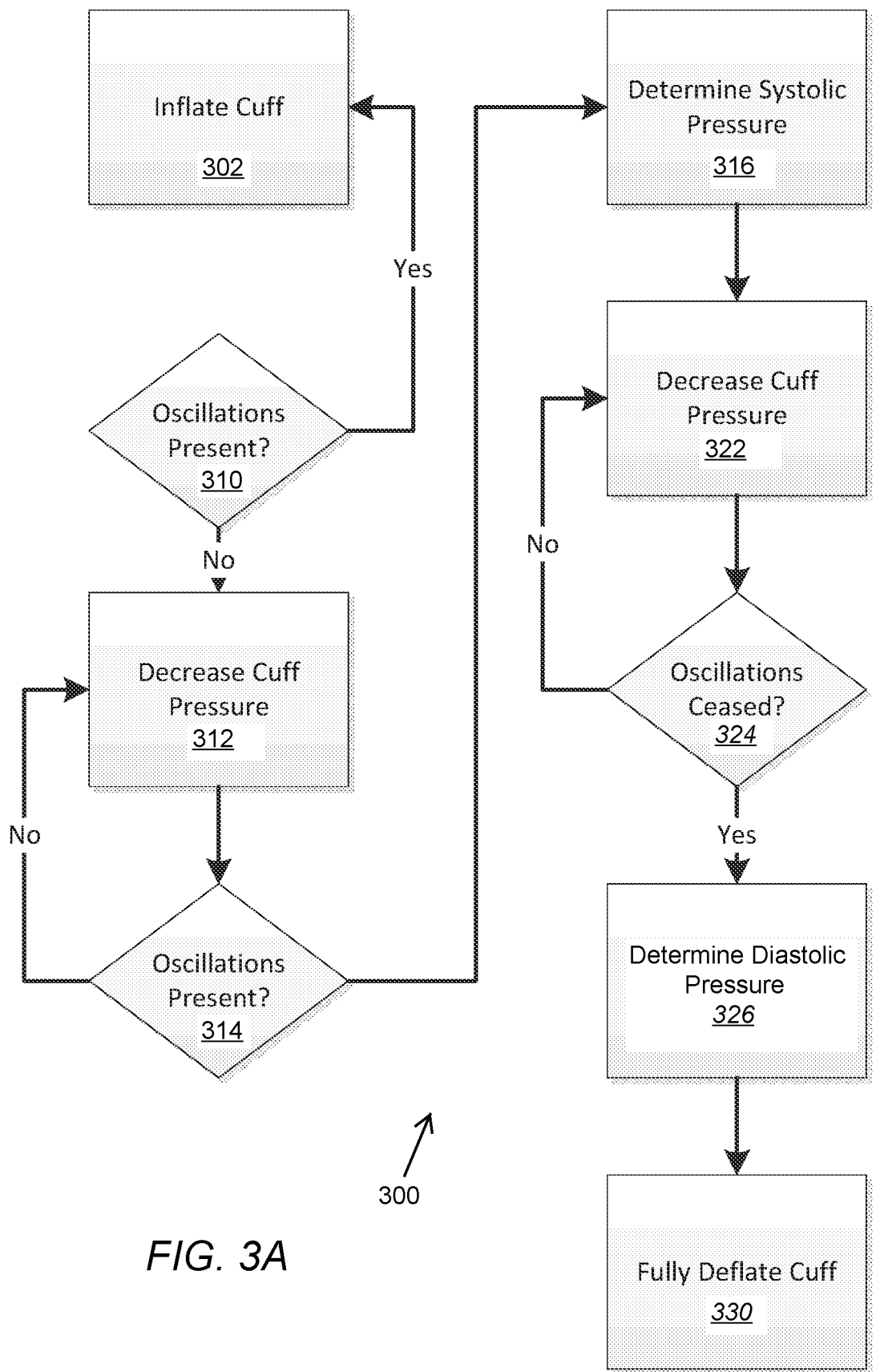
FIG. 3A is a block diagram illustrating an exemplary controller configuration of an system.
Figure 3B:
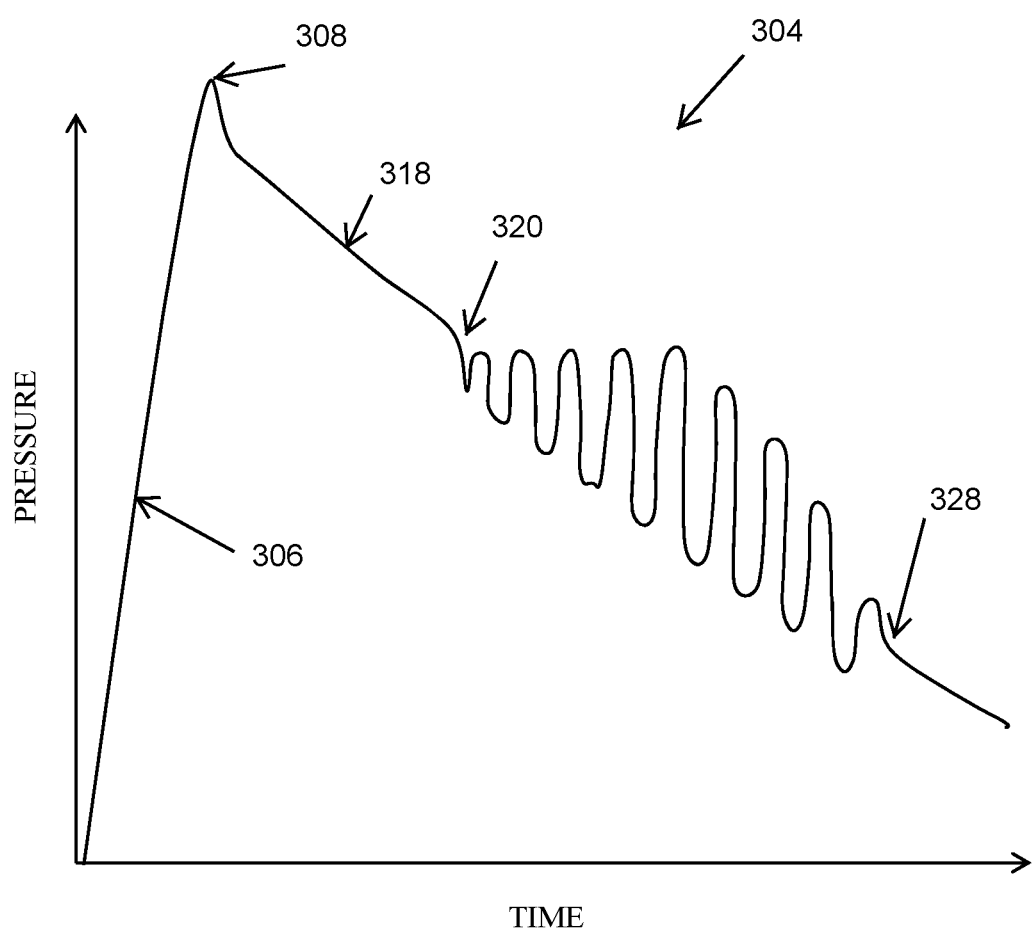
FIG. 3B is an exemplary pressure tracing.

In one example of control of the blood pressure measurement device, illustrated in FIG. 3A and corresponding pressure tracing in FIG. 3B, the basic operational process 300 involves inflation of the cuff 302 that is located in the housing and/or band of the device. This is depicted in the pressure tracing 304 in FIG. 3B as the initial increase in pressure 306. In some variations, cuff inflation 302 is performed to a specific level 308 that is pre-specified and/or is user-selectable in the control settings of the device. In some variations, the device controller may be configured to automatically adjust or suggest a specific inflation level based upon the user's prior blood pressure records, in order to decrease discomfort from excessive inflation levels.

In some variations, upon achieving the desired inflation level, the device may immediately check of the presence of blood pressure signal, such as a Korotkoff sound, a pressure waveform or oscillations 310, and if present, further inflate the device until such signal is no longer present, and/or also provide a user alert if high systolic pressures are identified. This may occur, for example, with a sensor error, or if the user is in a hypertensive crisis and should seek immediate medical attention.

Under typical conditions where a pressure signal is not identified upon achieving the initial inflation level, the device will begin to decrease the cuff pressure 312 and detect the onset of oscillations 314 or Korotkoff sounds in order to determine the systolic pressure 316. This is shown, for example, in FIG. 3B for an oscillometry-based device as the downward slope 318 of the pressure tracing 304, and the start of oscillations 320. In tonometry-based systems, the cuff pressure may be adjusted to achieve the desired pressure waveform, e.g. pressure amplitude. The decrease in cuff pressure 306 may be performed in a stepwise or continuous manner. The decrease may be linear in size or rate, or may be non-linear, e.g. the size or rate may depend on the current pressure, with larger decreases at high pressures, and lower decreases at lower pressures. In some variations, different rates may be provided before and after detection of the systolic pressure, and/or before and after detection of the diastolic pressure. In some variations, the decrease in pressure may be in the range of about 1 mm Hg/second to about 10 mm Hg/second, or about 1 mm Hg/second to about 5 mm Hg/second, or about 2 mm Hg/second to about 4 mm Hg/second, or about 2 mm Hg/second to about 3 mm Hg/second.

After the determination of the systolic pressure, the device will continue to decrease the cuff pressure 322 until the oscillations or Korotkoff sounds have ceased 324. This pressure point is then used to determine the diastolic pressure 326, and is depicted in tracing 304 as point 328. After this, the cuff can be deflated 330, either actively or passively. In tonometry-based systems, once the cuff pressure is adjusted to acquire the desired pressure waveforms, the cuff can be deflated.

Figure 4A:
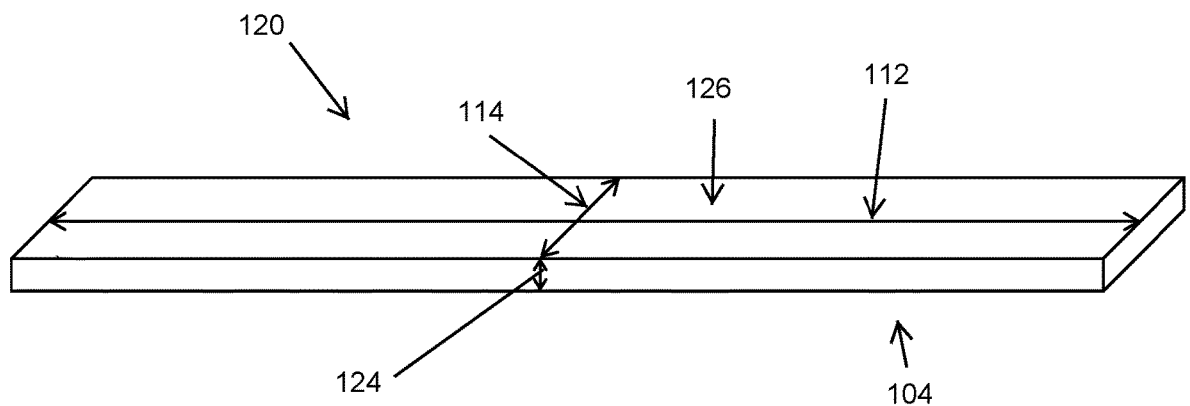
FIGS. 4A and 4B are perspective schematic views of an expandable member in a flat and circumferential configuration.
Figure 4B:
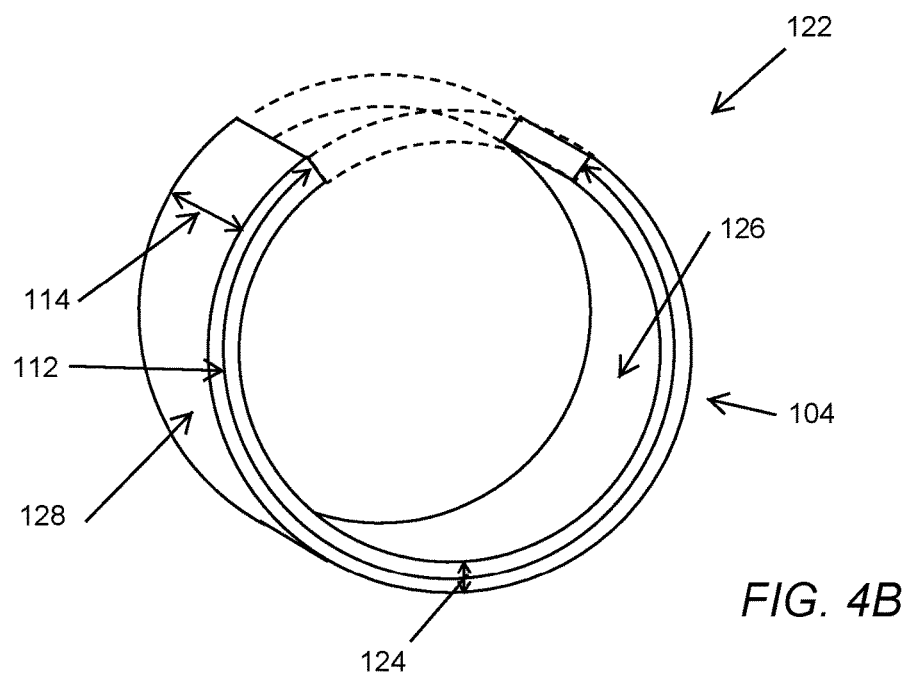

Referring back to FIGS. 1A and 1B, in referring to the band 104 of the device 100, as used herein, the length 112 of the band 104 is used to describe the circumferential dimension of the band 104, and the width 114 of the band 104 is the dimension of the band 104 along the longitudinal axis of the limb, from a proximal edge 116 to the distal edge 118 of the band 104. These dimensions may be used to describe the band 104 independent of whether the band 104 is in a flat configuration 120 as shown in FIG. 4A, or in a curved or circumferential configuration 122 as shown in FIG. 4B. FIGS. 4A and 4B also depict the height or vertical dimension 124 of the band 104. The band 104 may be further characterized as having an external surface 126 and an internal surface 128 that is configured to contact the skin.

Figure 5:
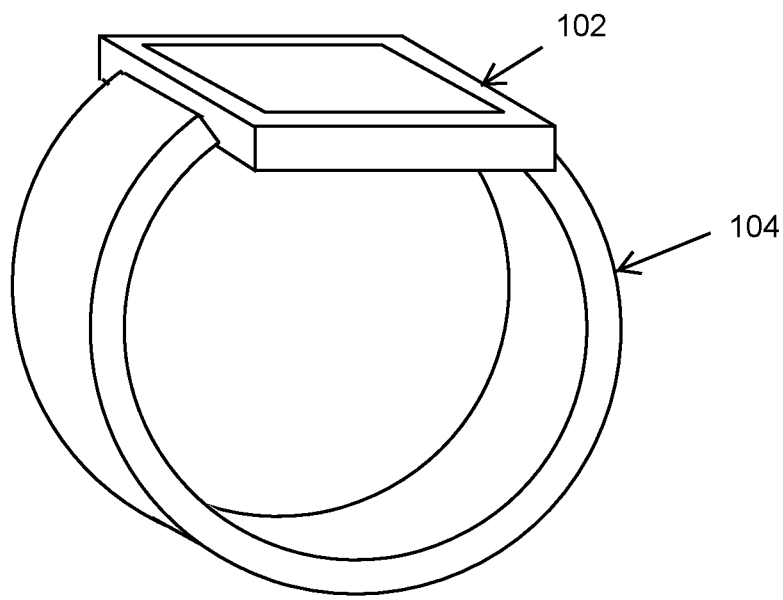
FIG. 5 is a perspective schematic view an exemplary system with an expandable member and a housing with a display.
Figure 6:
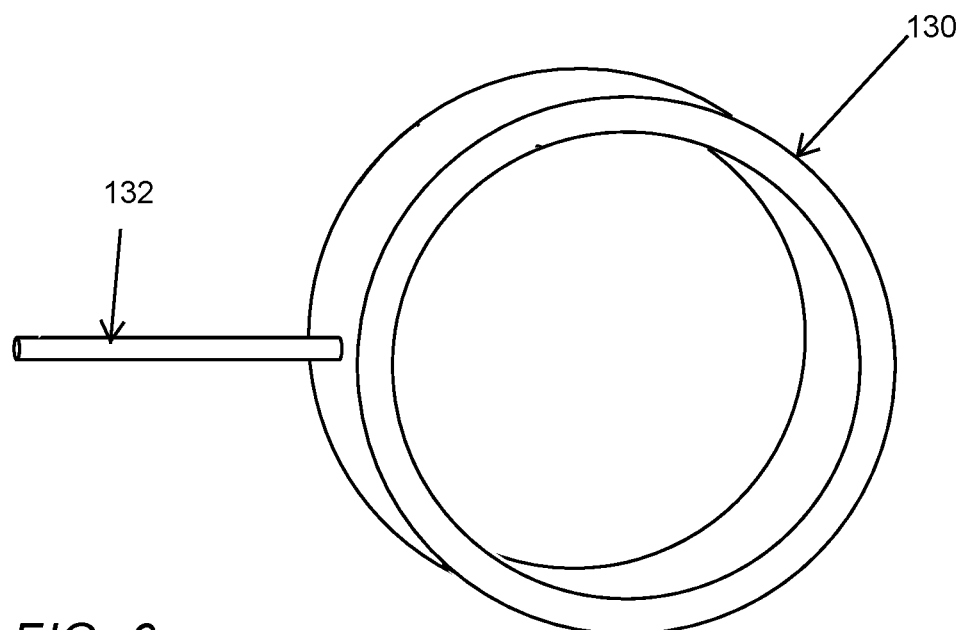
FIG. 6 is a perspective schematic view of a circumferential expandable member and conduit.

As indicated earlier with respect to FIGS. 1A and 1B, the housing 102 and/or band 104 of the device 100 comprise an expandable member which is configured to apply pressure and sense pressure levels, waveforms, and/or oscillations. The expandable member may be an inflatable structure configured to be inflated by a pump, but in other variations, the expandable member may comprise an motorized, articulated mechanism configured to mechanical expand and contract, e.g. scissor-linkages coupled to a micromotor or screw drive actuator, for example. In some variations, the various components described in FIG. 2A may be provided in the housing 102 and/or band 104, depicted in FIG. 5, but in other variations, as shown in FIG. 6, a distinct housing may not be provided with the band 130. The various components described in FIG. 2A may be provided in a separate housing that may be attached via a conduit 132 to the band 130, though in some variations, one or more components may be located in the band 130, such as the pressure sensor.

Referring to back to FIGS. 4A and 4B, in some examples, the length of the band or expandable member may be in the range of about 100 mm to about 400 mm, or about 200 mm to about 300 mm or about 225 mm to about 275 mm, for example. In some variations, the total length of the expandable member is less than the total length of the band. In some further variations, the total length of the expandable member may be about 10-80% of the total length of the band, or about 20-60%, 30-60%, or 20-50%. The reduced size of the expandable member relative to the band may provide a greater range of adjustability to band for the wearer's anatomy, or may be sufficient for the desired range of operability for blood pressure measurement. The width 114 may be in the range of about 5 mm to 45 mm, about 10 mm to about 40 mm, or about 20 mm to about 30 mm, for example, in the deflated state, the height of the expandable member may be less than 1 mm, 2 mm, 3 mm, 4 mm, 5 mm, for example, or may be in the range of about 0.5 mm to about 5 mm, about 1 mm to about 5 mm, about 1 mm to about 4 mm, about 2 mm to about 4 mm, about 1 mm to about 3 mm, or about 2 mm to about 3 mm, for examples. The wall thickness of the expandable member may be in the range of about 0.05 mm to about 1 mm, about 0.1 mm to about 0.9 mm, about 0.1 mm to about 0.5 mm, about 0.05 mm to about 0.7 mm, about 0.05 mm to about 0.5 mm, for example. The expandable member may comprise one or more materials, including but not limited to thermoset polymer, a thermoplastic polymer, a polyolefin, polyethylene, low density polyethylene, medium density polyethylene, high density polyethylene, a modified polyethylene (including maleated polyethylene), polypropylene, a urethane, a polyurethane, a polyamide (including homopolymer and co-polymers), nylon (including nylon-6,6, nylon-11, nylon-12), a polyolefin, polypropylene, an elastomer, silicon, for example. The material may be an extruded material, a woven material, or a multi-layer material, for example.

Various exemplary configurations of the expandable member are described in greater detail below. The orientations of these various configurations may be best understood in reference to FIG. 1A, which depicts the orientations of the band 104 that incorporates the expandable member and length 112, width 114 and/or cross sectional view 134 orientations, as referenced below. Also, although not shown, the expandable members may comprise at least one opening to facilitate inflation into the expandable member. In some variations, the opening is also used to deflate the expandable member, but in other variations, at least one separate deflation opening is provided in the expandable member. The inflation and/or deflation openings may be provided at a longitudinal end of the expandable member, a proximal and/or distal edge of the expandable member, and/or the outer surface and/or inner surface of the expandable member. The openings located on the edges or inner/outer surfaces of the expandable member may be located anywhere along the length of the expandable member. In some embodiments, the openings are located symmetrically between the longitudinal ends of the expandable member, while in other embodiments, the openings are located asymmetrically between the longitudinal ends of the expandable member.

Figure 7A:
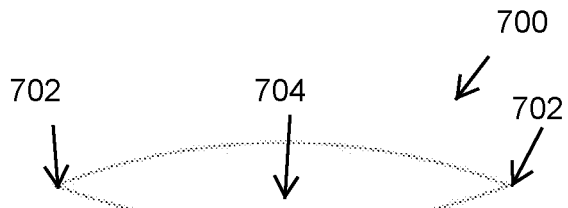
FIGS. 7A and 7B are schematic cross-section and perspective views of an exemplary expandable member comprising a single expandable cell.
Figure 7B:
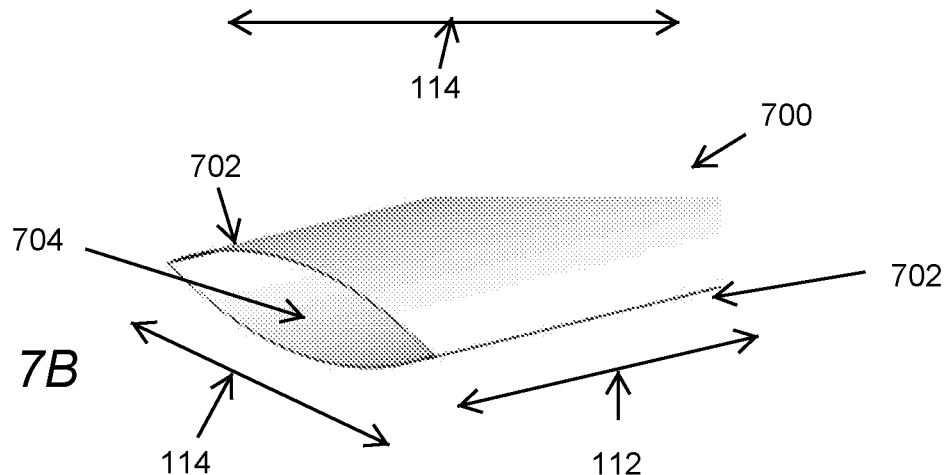

FIGS. 7A and 7B depict one example of an expandable member 700, comprising a single, generally rectangular inflatable shape 700 which is depicted in the partially inflated state. As can be seen, the expandable member exhibits less expansion and has a tapered configuration towards its edges 702, compared to its central region 704. In some variations, this configuration exhibits reduced a reduced skin or surface contact because of the reduced expansion exhibited at the edges 702.

Figure 8A:
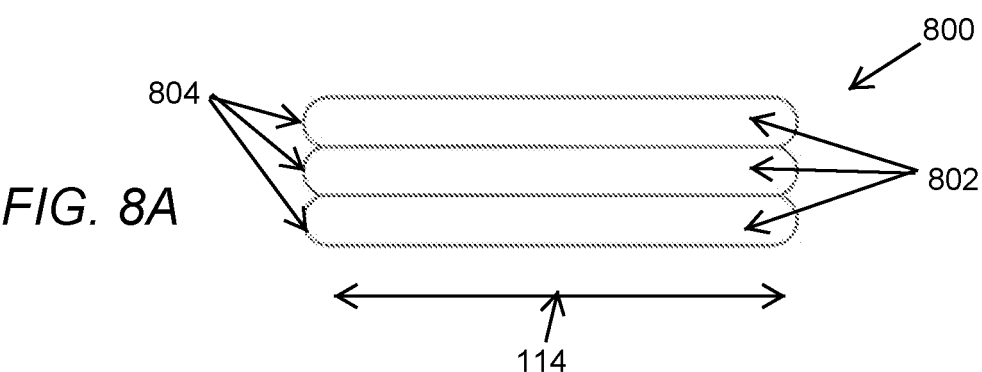
FIGS. 8A and 8B are schematic cross-section and perspective views of an exemplary expandable member comprising a multiple expandable cells in a stacked configuration.
Figure 8B:
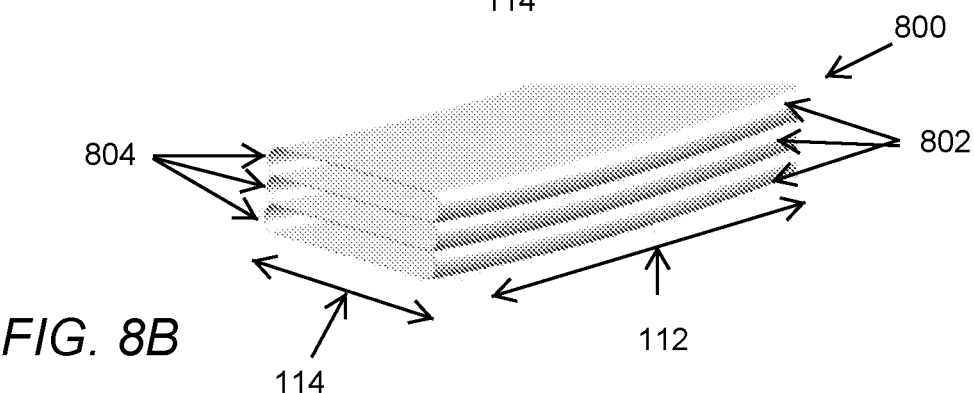

FIGS. 8A and 8B depict another example of an expandable member 800, comprising a stack of inflatable or expandable rectangular cells 802 with rounded edges 804 rather than tapered edges as provided in the expandable member 700 in FIGS. 7A and 7B. It is hypothesized that by providing rounded edges 804, greater expansion may be provided about the edges 804. In conjunction with the stacked configuration, a cumulative amount of edge expansion may be provided, compared to a single expandable cell. The contacting surfaces of the cells 802 may be attached in a variety of ways, including adhesives, heat melding, ultrasonic welding, and the like, or may be extruded or injection molded in a single piece. Although three cells 802 are depicted in FIGS. 8A and 8B, in other variations, the expandable member may comprise a stack of cells in the range of 2 to 5 or more, 1 to 3, or 2 to 4, for example. In some further variations, the cells 802 may also be sectioned across the width 114 of the expandable member, in the range of 2 to 4, 2 to 3, or 1 to 3, for example.

Figure 9A:
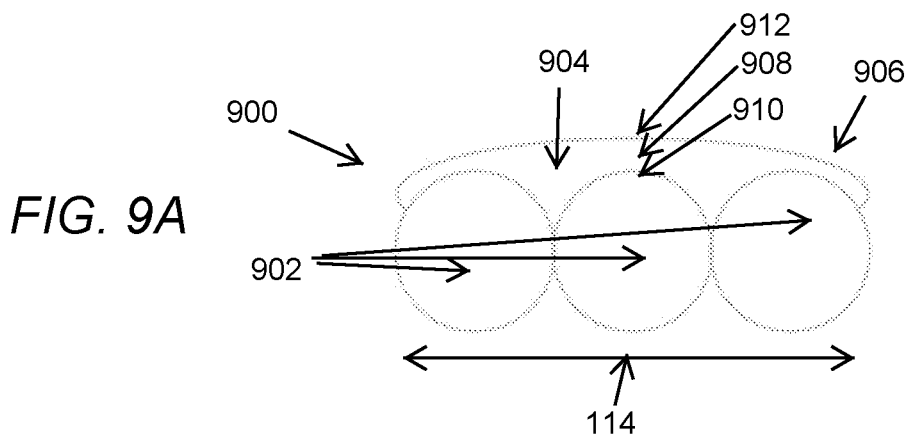
FIGS. 9A and 9B are schematic cross-section and perspective views of an exemplary expandable member comprising multiple expandable cells in a sectioned configuration and a sensing member.
Figure 9B:
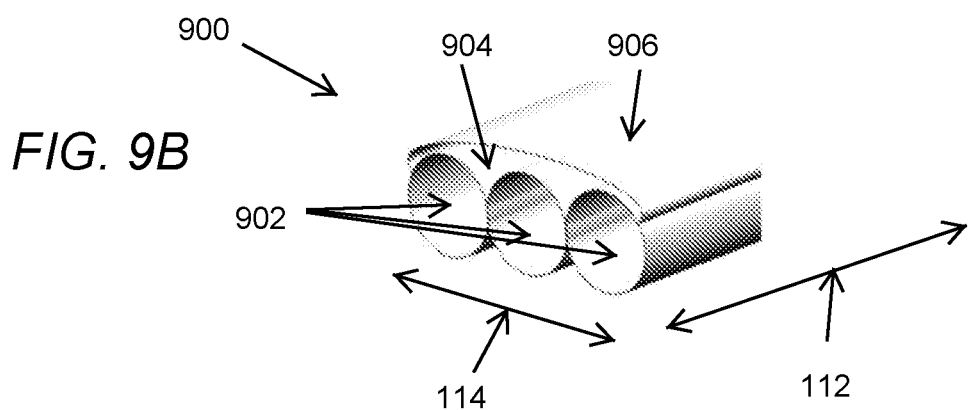

FIGS. 9A and 9B depict another example of an expandable member 900, comprising three main expandable cells 902, which are coupled together in a side-by-side fashion along their lengths 112. In their maximum expanded state, the cylindrical cells 802 may have a diameter in the range of about 1 mm to about 10 mm, sometimes about 2 mm to about 8 mm, about 3 mm to about 6 mm, about 4 mm to about 6 mm, for example. In this particular example, the enlarged diameter of the cells 902 may permit an increased vertical dimension expansion size, but may reduce the longitudinal flexibility of the expandable member 900. In some variations, the increased height of the cells may result in inward creases or pinching in of the cells 902 when it is inflated around a wrist or limb, which may or may not affect the comfort or accuracy of the device during use. In some further variations, to provide a more uniform skin or surface contact, an expandable sensing cell 904, may be provided over the superior surface of the expandable member 900. The sensing cell 904 may be configured with an increased width across a substantial width of the expandable member 900, but has a reduced vertical dimension relative to the cells 902. In some variations, a device with this expandable member 900 may be configured to sense only in sensing cell 904, but may also be configured to sense in one or more of the lower cells 902. In some variations, the sensing cell 904 may have a width 114 that is in the range of about 10% to about 100%, about 50% to about 100%, about 40% to about 90%, or about 80% to about 100% of the width of the expandable member, The height 908 of the sensing cell 904, as measured from a point of maximum height 910 of main cells 902 to a corresponding point of maximum height 912 of the sensing cell 904, may be in the range of about 1 mm to about 8 mm, about 2 mm to about 6 mm, about 3 mm to about 5 mm, or about 2 mm to about 4 mm, for example. The height 908 of the sensing cell 904 may also be characterized as a percentage of the height of the main cells 902, and may in the range of about 10% to about 80%, about 20% to about 60%, about 30% to about 50%, about 20% to about 40%, for example. Although the sensing cell is described herein with respect to expandable member 900, the sensing cell may also be provided on the other embodiments described herein, including but not limited to the exemplary expandable members 800, 1000, 1100, 1200, 1300, 1400, 1500, 1550, 1600, 1700, 1800, 1900, 2000, and 2100, for example. Also, although the depicted expandable member 900 comprises three identical cylindrical expandable cells 902, in other variations, the number of cylindrical cells may be different and in the range of about 2 to 5 or more, 3 to about 5, or 2 to about 4, for example. The expandable cells need not be identical, and each may have a different size or cross-sectional shape, including square, oblong, teardrop, triangular, columnar, pentagonal, hexagonal, or other polygonal shape, for example.

Figure 10A:
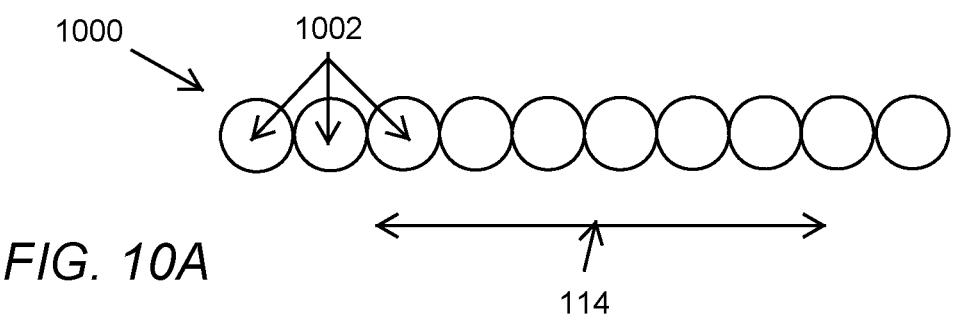
FIGS. 10A and 10B are schematic cross-section and perspective views of another exemplary expandable member comprising multiple cylindrical expandable cells in a sectioned configuration.
Figure 10B:
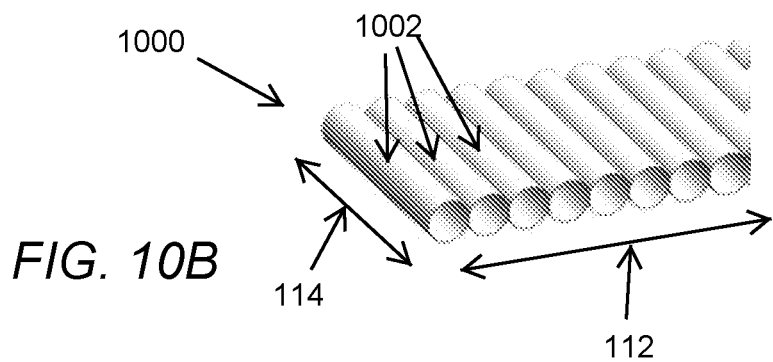
Figure 11A:
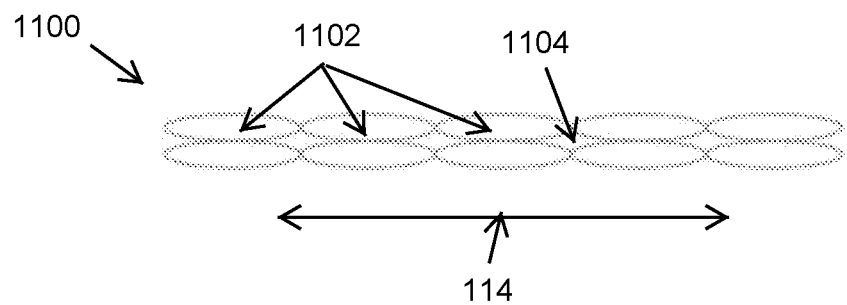
FIGS. 11A and 11B are schematic cross-section and perspective views of an exemplary expandable member comprising multiple oblong expandable cells in a stacked and sectioned configuration.
Figure 11B:
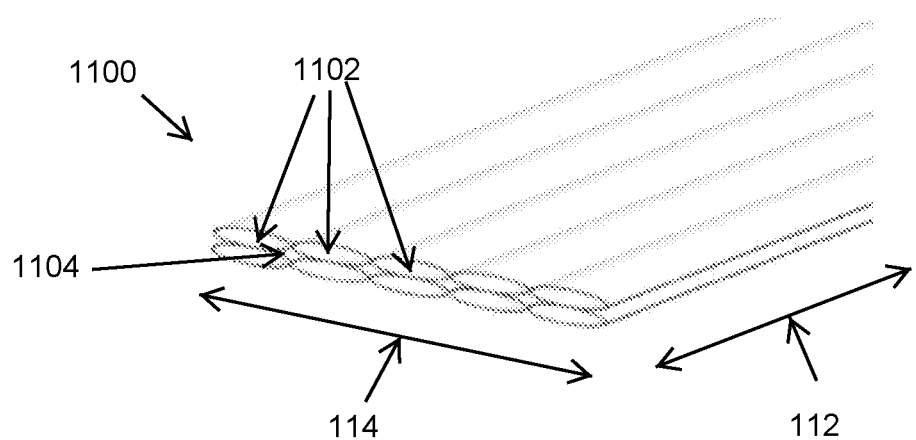

In another embodiment, depicted in FIGS. 10A and 10B, the expandable member 1000 may comprise a plurality of attached elongate cells 1002, wherein the elongate cells comprise lengths 1004 that are aligned along the widths 114 of the expandable member 1000. In some variations, the use of expandable cells 1002 with an orientation that is orthogonal to the general orientation of the expandable member 1000, the creasing or pinching in may be reduced or eliminated. Although the depicted expandable member 1000 comprises repeating identical cylindrical expandable cells 1002, in other variations, the expandable cells 1002 of expandable member 1000 need not be identical, and each may have a different size or cross-sectional shape, including cylindrical, square, oblong, teardrop, triangular, columnar, pentagonal, hexagonal, or other polygonal shape, for example. As with expandable member 900, the number of cylindrical cells for expandable member 1000 may vary and be in the range of 5 to 25 or more, 10 to 30, 15 to about 25, 20 to 30, or 20 to 40, for example. FIGS. 11A and 11B depict another embodiment of the expandable member 1100, comprising elongate expandable cells 1102 that are stacked vertically and sectioned across the width 114 of the expandable member 1100. In this particular embodiment, the expandable cells 1102 comprise an oblong cross sectional shape, with a height to width height ratio that is about 1:5. In other variations, the height to width ratio may be in the range of about 1:1 to about 1:20, about 1:2 to about 1:10, about 1:3 to about 1:8, or about 1:5 to about 1:10, for example. The stacked and sectioned configuration, or matrix configuration of this expandable member 1100 may be characterized as a 2×5 elongate configuration, with the elongate expandable cells 1102 stacked two cells high and 5 cells across the width 114 of the expandable member 1100. In other embodiments, the expandable member may comprise a stacking configuration in the range of about 2 units to about 10 units, about 2 units to about 8 units, or about 3 units to about 6 units, for example. In this example, each level of the stacked cells is horizontally aligned with the stacked cells of the adjacent levels, and each section is vertically aligned with the adjacent sectioned cells. This alignment configuration may be characterized as having a zero horizontal offset and a zero vertical offset, respectively, but in other embodiments, a horizontal and/or a vertical offset may be provided. In some variations, the offsets may be characterized based upon the relative unit size, e.g. each layer may be offset by 0.5 unit width, or every other section may be offset by 0.5 unit height. In some variations, unit offsets of 0.5 unit width or height may be used to reduce the cross-sectional shape or size of the intercell gaps 1104 that may be present in the expandable member. In other variations, the unit offset in one or more directions may be in the range of about 0 units to about 0.99 units, about 0.1 units to about 0.9 units, about 0.2 units to about 0.8 units, about 0.3 units to about 0.7 units, about 0.4 units to about 0.6 units, or 0.5 units.

Although the preceding exemplary embodiment comprise elongate expandable cells of various cross sectional shapes that extend from one end to the other end of the length of the expandable member, in other embodiments, the elongate member may comprise smaller or shorter expandable cells that are configured to be attached end-to-end, or side-to-side. Thus, the configuration of the expandable member may be a Z by W by L matrix configuration, based upon Z unit stacking and W width sections and L length sections, with or without any unit offsets along any of the dimensions. For example, an expandable member with a length of 250 mm may comprise elongate cells with a length of 125 mm forming two longitudinal sections that are configured in an end-to-end fashion to achieve a net length of 250 mm.

Figure 12A:
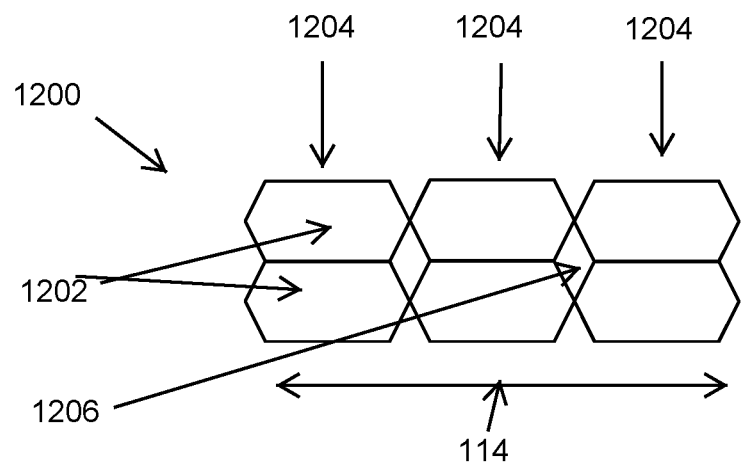
FIGS. 12A and 12B are schematic cross-section and perspective views of an exemplary expandable member comprising multiple expandable cells in a stacked and bi-sectioned configuration.
Figure 12B:
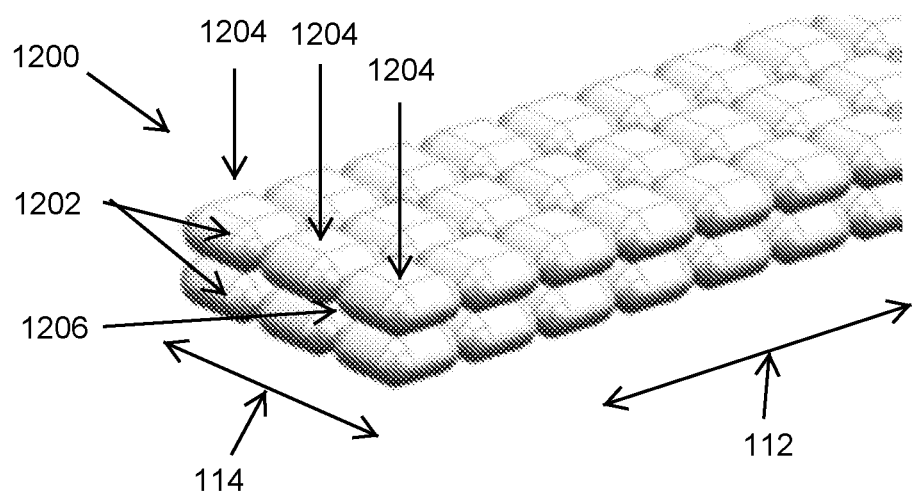

Likewise, other embodiments may comprise non-elongate expandable cells shapes. In FIGS. 12A and 12B, for example, the expandable member 1200 comprises a 2×3×L matrix configuration, with each expandable cell 1202 comprising a box-like shape. Each cell 1202 has a flattened hexagonal shape on a cross-section transverse to the length 112 or width 114 dimension of the expandable member 1200, and a square shape with chamfered corners, or otherwise octagonal or polygonal cross sectional shape on a transverse cross section along the vertical dimension. In this particular embodiment, the expandable cells 1202 comprise the same length and width, and a height that is about half of the length or width. The width sections 1204 of the expandable member 1200 have a zero vertical offset and form diamond-shape intercell gaps 1206 In some variations, the expandable cells may have a length and/or width in the range of about 2 mm to about 15 mm, about 3 mm to about 10 mm, about 5 mm to about 15 mm, or about 5 mm to about 10 mm, for example, and a height in the range of about 1 mm to about 10 mm, about 2 mm to about 8 mm, about 3 mm to about 6 mm, for example. Other variations may have other matrix configurations similar to the ranges described for the exemplary expandable member 1100 with respect to the stacking, width sections and offsets, and may have length configurations as described in the ranges for exemplary expandable member matrix configuration may have other matrix configurations than the 2×3×L matrix configuration illustrated in FIGS. 12A and 12B. The length component of the matrix may be in the ranges as described for exemplary expandable member 1100 above.

Figure 13A:
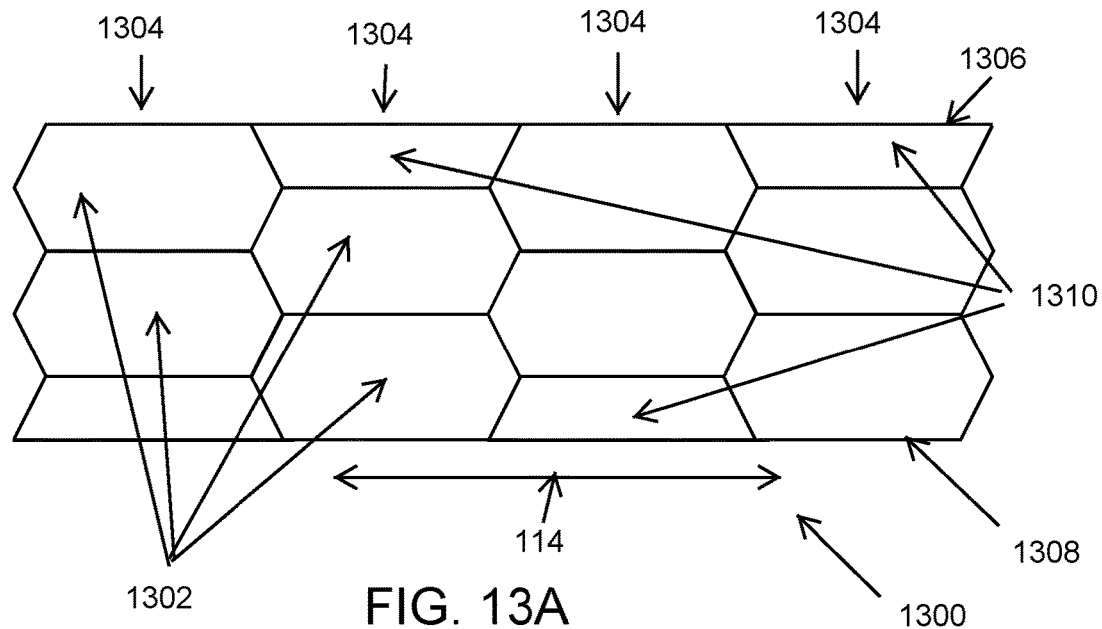
FIGS. 13A and 13B are schematic cross-section and perspective views of an exemplary expandable member comprising multiple elongate hexagonal expandable cells in a stacked and sectioned configuration.
Figure 13B:
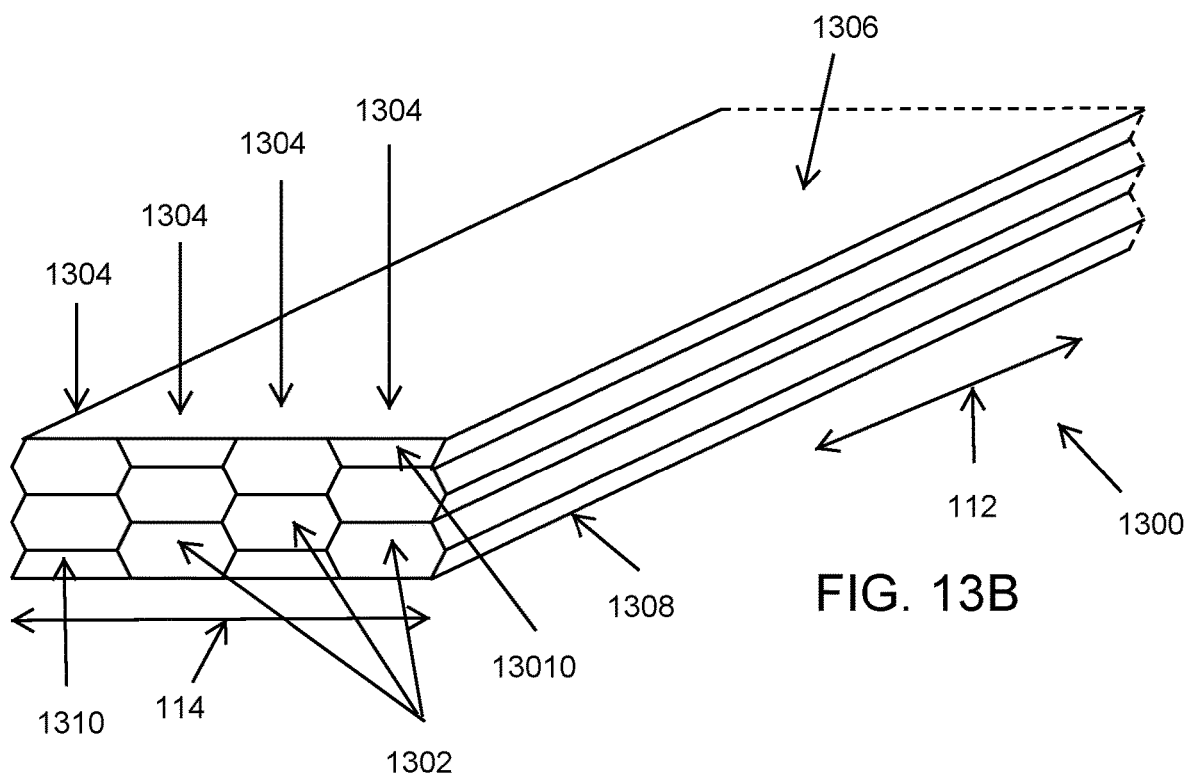

The embodiment depicted in FIGS. 13A and 13B, depicts an alternate embodiment with a repeating cell geometry without any intercell gaps. In this particular example, the expandable member 1300 comprises hexagonal cells 1302 in a 2.5×4 matrix configuration and an alternating 0.5 unit vertical offset for the width sections 1304. As a result of the vertical offset, each width section 1304 has an interfit relationship with the adjacent width sections 1304, and therefore no intercell gaps are present. In order to maintain a planar superior and inferior surface 1306 and 1308, respectively, some partial cell, or half shape cells 1310 are present in the width sections 1304.

Figure 14A:
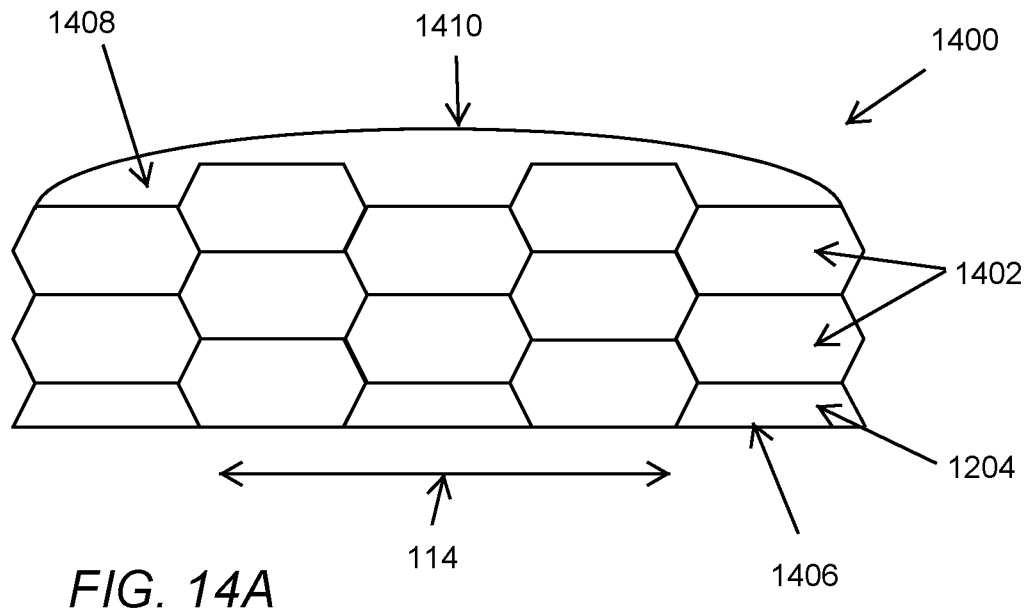
FIGS. 14A and 14B are schematic cross-section and perspective views of another exemplary expandable member comprising multiple elongate hexagonal expandable cells in a stacked and sectioned configuration, and a sensing cell.
Figure 14B:
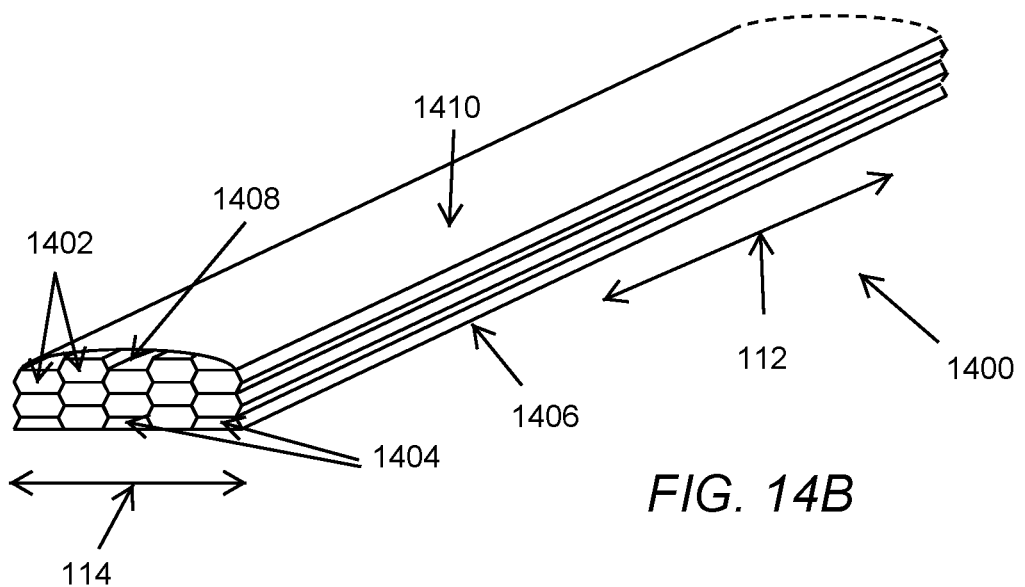

In other embodiments, the superior or contact surface of the expandable may be non-planar. For example, in FIGS. 14A and 14B, the expandable member 1400 comprises a plurality of hexagonal or half-hexagonal elongate cells 1402 and 1404, respectively, with vertical offsets. While half-hexagonal cells 1404 are provided long the inferior surface 1406 of the expandable member 1400, full size hexagonal cells are provided elsewhere, which results in non-planar configuration superiorly. In some variations, an optional expandable sensing cell 1408 may be provided on the superior surface 1410, similar to the various configurations of the expandable sensing cell described for the expandable member 900 described in FIGS. 9A and 9B.

Figure 15A:
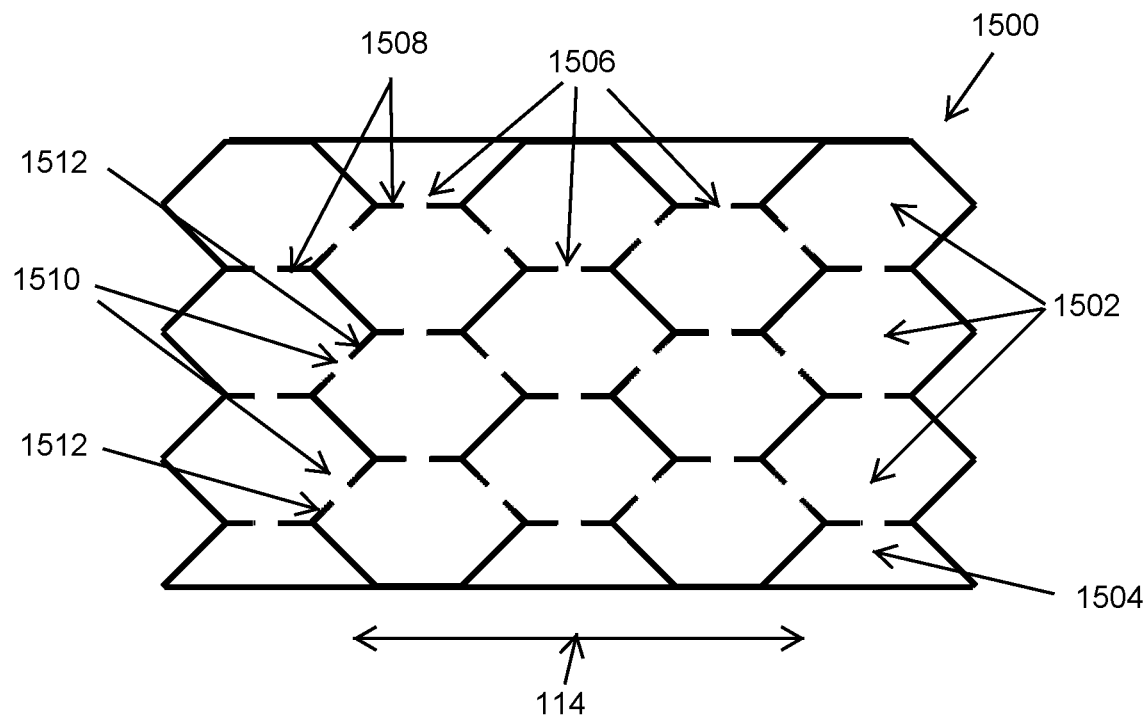
FIGS. 15A and 15B are schematic cross-sectional views of hexagonal expandable cells in a stacked and sectioned configuration, with vertical and side intercell openings, and only vertical intercell openings, respectively.
Figure 15B:
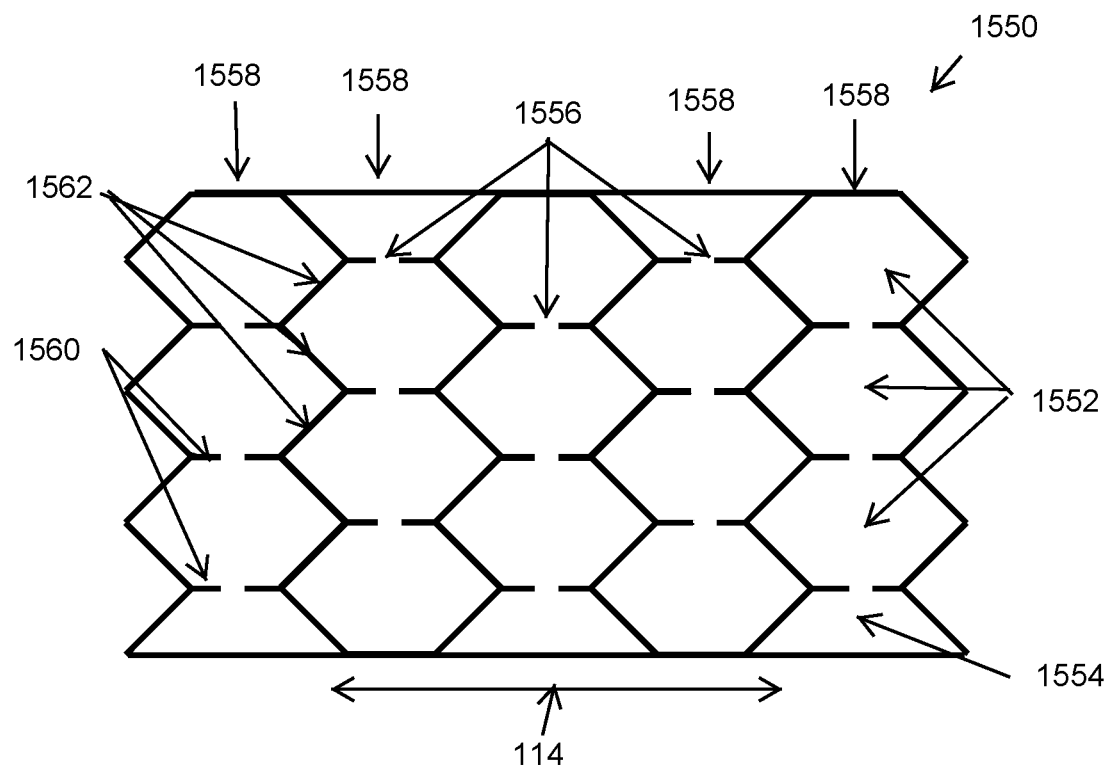

Although not depicted in the FIGS. 8A to 14B, the in some variations, two or more cells of the expandable member may be interconnected by providing openings in the cell walls between the cells. In some variations, all of the cells are interconnected with adjacent cells, which may allow pressure equalization throughout the expandable member. In other variations, the expandable member may be configured with multiple subsets of cells, wherein the cells within a subset are interconnected, but cells are not interconnected with cells of other subsets. These openings may be formed by mechanical drilling, laser or heat melting, or heat molding, for example. The openings may or may not be reinforced, with an increased thickness of material around the opening, compared to the thickness of the rest of the cell wall. Referring to FIG. 15A, for example, an expandable member 1500 comprises hexagonal cells 1502 and half-hexagonal cells 1504 wherein each cell has at least one wall opening 1506, such that all of the cells 1502, 1504 are in fluid communication with each other, and permit pressure equalization throughout the expandable member 1500. In this example, wall openings 1506 are provide in the horizontal walls 1508 of the expandable member 1500, and as well as wall openings 1510 in the angled walls 1512. FIG. 15B depicts another example wherein the expandable member 1550 comprises hexagonal and half-hexagonal cells 1552, 1554, respectively. Here, wall openings 1556 between cells along the same column or subset 1558, but not between different columns or subsets, e.g. the wall openings 1556 are provided in the horizontal cell walls 1560, but not in the side or angled cell walls 1562.

In embodiments of the expandable member comprising multiple cell subsets, each subset may be configured with its own pressure sensor, and may or may not be individually expandable or inflatable. In some variations, the device may be configured to expand some or all of the cell subsets during use. The cell subsets used may be expanded simultaneously, or serially, and/or permit expansion or inflation to different levels between the subsets. In some embodiments, the sensor output from each subset may be used to select the sensor output with the greatest signal strength or signal range, and/or may be used to more accurately identify the systolic and/or diastolic pressures, e.g. requiring two adjacent cell subsets, or certain cell subsets to detect the onset and/or cessation of sensor signals for the identification of the systolic and/or diastolic blood pressure. In some variations, use of multiple sensors in different cell subsets may at least partially enhance the accuracy of systolic blood pressure and/or diastolic blood pressure measurement.

Figure 16A:
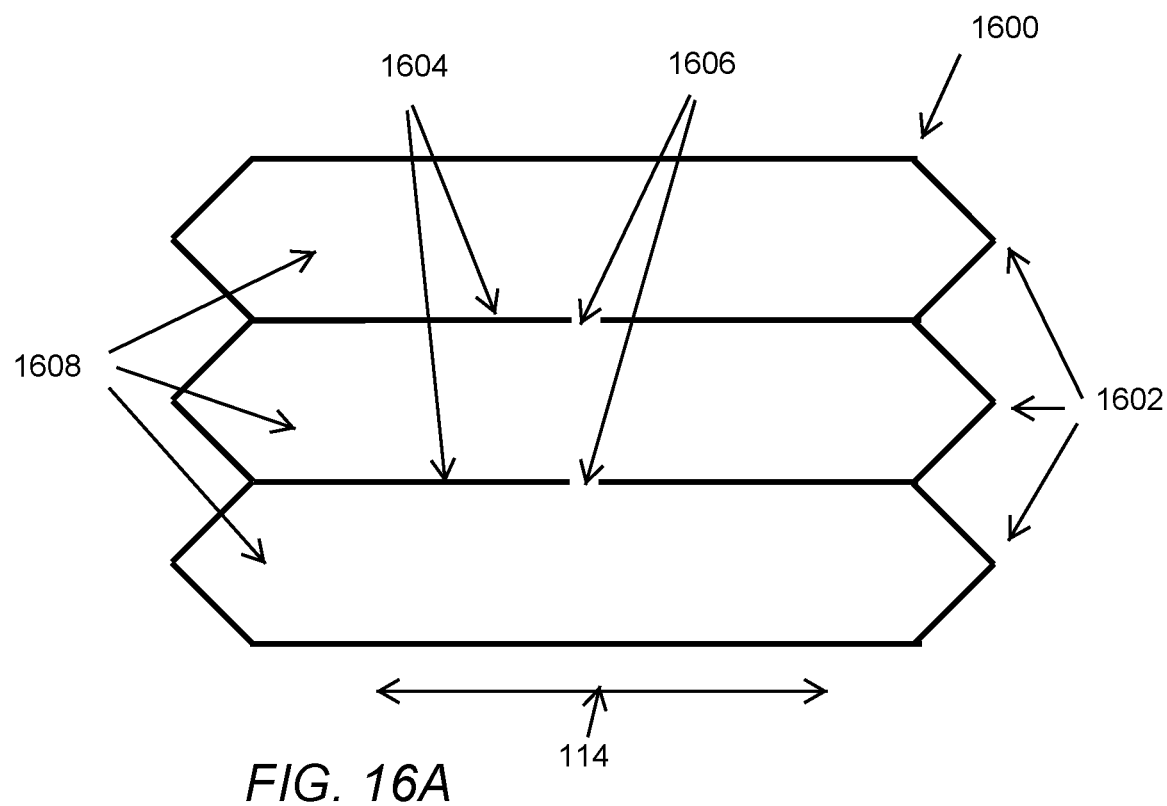
FIGS. 16A and 16B are schematic cross-sectional views of expandable cells in a stacked configuration, with outwardly and inwardly configured folds, respectively.
Figure 16B:
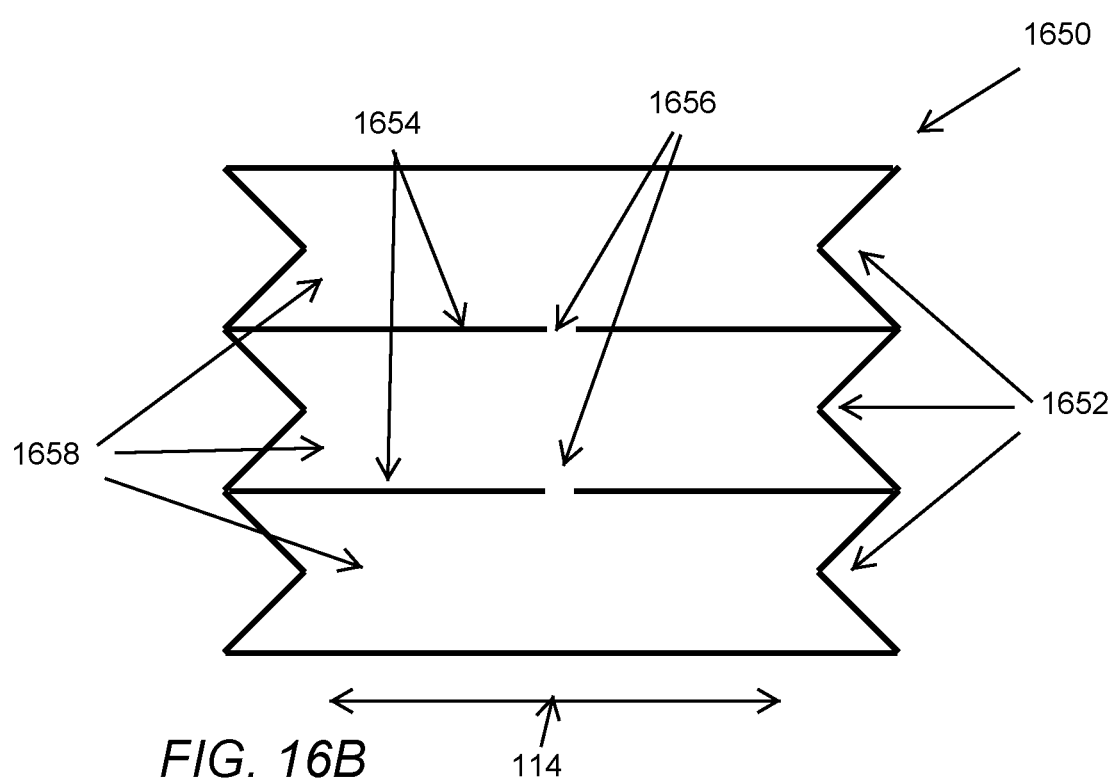

In some embodiments, the expandable member may comprise rigid or semi-rigid horizontal walls or side walls. In some variations, this may augment or enhance the vertical displacement of the expandable member at its edges, and may provide sufficient vertical displacement such that multiple sections of cells are not required across the width of the expandable member. As shown in FIGS. 16A and 16B, exemplary expandable members 1600, 1650 with rigid or semi-rigid walls may expand and collapse in an accordion like manner, and may be configured with outer edges 1602, 1652 that fold outwardly or inwardly, respectively. In the depicted examples, the horizontal walls 1604, 1654 comprise wall openings 1606, 1656 to permit fluid communication and pressure equalization between the cells 1608, 1658, respectively.

In some of the embodiments described herein, the structural properties or configuration may be consistent along the length or circumference of the expandable member, but in other embodiments, one or more local regions of the expandable member may have different structural characteristics or features. For example, in FIGS. 17A and 17B, the expandable member 1700 comprises first and second subsets of elongate cell members 1702, 1704 with longitudinal lengths aligned with the longitudinal length 112 of the expandable member 1700. In addition, third and fourth subsets of elongate cell members 1706, 1708 may be provided in a local region 1710' along the expandable member 1700. In some embodiments, the location of the local region may be configured to facilitate detection of blood pressure signal with respect to an anatomical location. In the embodiment depicted in FIG. 17B, for example, the local region 1710 of cell members, which corresponds to the third and fourth subsets of cell members 1706, 1708, are located with respect to the length 112 of the expandable member 1700 that facilitates measurement of blood pressure signal at the radial artery of the wrist. In other variations, the local region may be configured to measure pressures at a different limb or limb location, e.g. ulnar artery, brachial artery, femoral artery, tibial artery, dorsalis pedis artery, for example, and in some variations, multiple local regions of cell members may be provided and configured to measure different anatomical locations, or the same anatomical location but under different device orientations, e.g. with the housing on the posterior or anterior wrist, or between the left and right wrists. In some variations, the cells of the local region may have the same orientation as the cells comprising the general region 1712, but in other examples, as shown in FIG. 17A, the cell subsets 1706, 1708 of the local region 1710, may have a different or orthogonal orientation with respect to the cell subsets 1702, 1704 of the general region 1712.

In some embodiments, the general region 1712 of the expandable member 1700 may be located on the contact surface of the expandable member 1700, and the local region 1710 may be located on the outside, while in other embodiments, the local region 1710 may be located on the contact surface, with the general region 1712 having a relative outer position relative to the local region 1710. With the former configuration, a rigid or taut backing layer may be provided so that the expansion or inflation of the local region 1710 produced a force or displacement toward the user's limb, through the intervening general region 1712, rather than outward.

Figure 18:
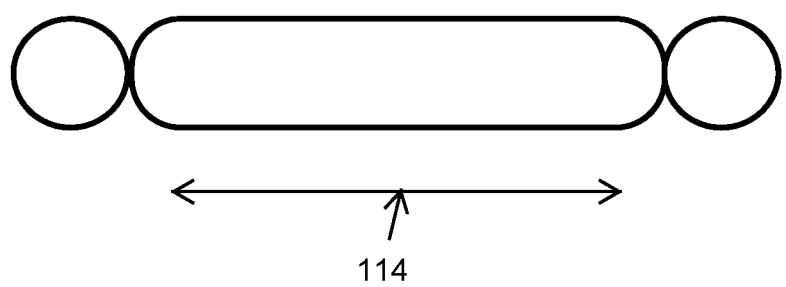
FIG. 18 depicts a schematic cross-sectional view of an expandable member comprising expandable edge support cells.

In some embodiments of the expandable member, is hypothesized that some cells or cell shapes may exhibit some rolling or shearing effect when inflated, such that the cell may shift or displace toward its proximal or distal edges during use. In some variations, to counter this effect, the expandable member may be configured with multiple cells across the width of the expandable members, which may be inflated with different pressures to counteract the effect of a narrow cuff, e.g. a cuff with a width of less than 50 mm. In the example depicted in FIG. 18, the expandable member 1800 comprises a first end cell 1802 and a second end cell 1804, and a middle cell 1806 therebetween. During use, cells 1802 and 1804 may be inflated to a higher pressure than the middle cell 1806, which may counteract any displacement bias during inflation. The higher pressures in cells 1802, 1804 may or may not be equal. In the specific example, depicted in FIG. 18, end cells 1802, 1804 comprise the same circular shape that is different from the oval shape of the middle cell 1806, but the end cells and middle cell(s) may have any of a variety of shapes and sizes (absolute and relative) as described herein with respect to other exemplary embodiments.

Figure 19:
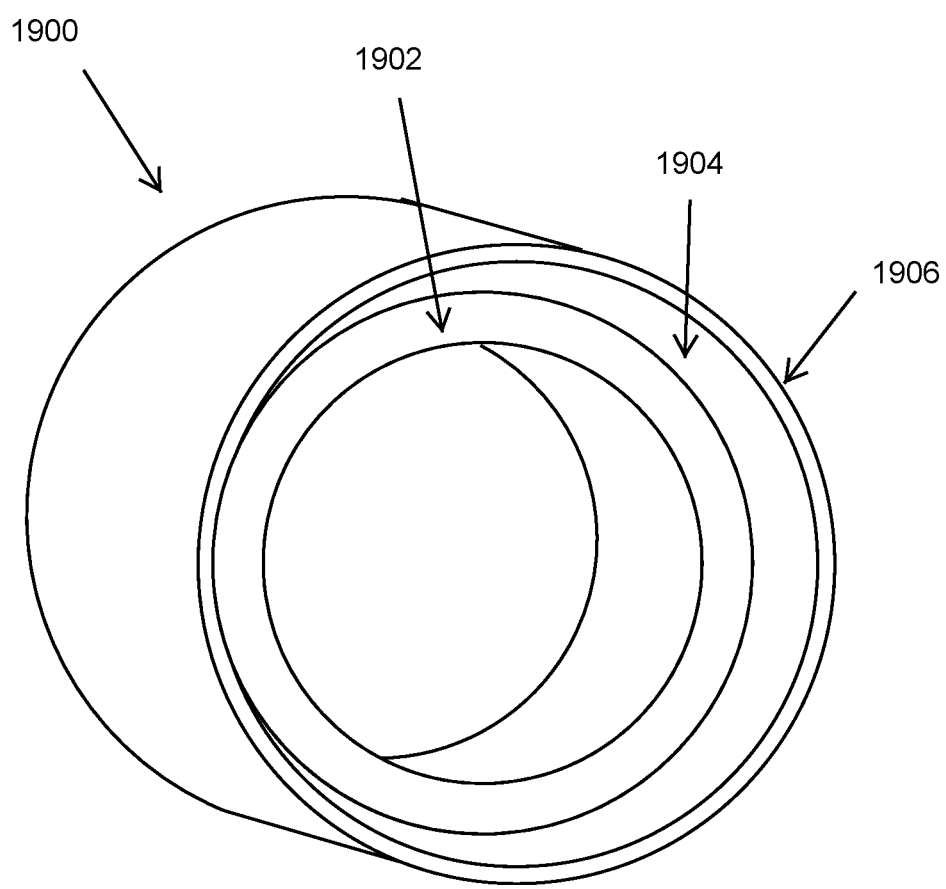
FIG. 19 is a perspective schematic view of an exemplary system with an expandable member located on a frame member.

As noted with respect to some embodiments above, in some examples of the blood pressure measurement device, the device may further comprise a support member to facilitate the application of force by the expandable member. In FIG. 19, for example, the device 1900 comprises an expandable member 1902 that is mounted on an inner surface 1904 of a support member 1906. The support member may comprise rigid or semi-rigid materials, including but not limited polyethylene terephthalate (PET), high density polyethylene (HDPE), polyvinyl chloride (PVC), polypropylene (PP) and polystyrene, or a metal, for example. The support member 1906 may comprise a single structure or may comprise a plurality of linked or articulated structures, similar to a metal watchband, for example. The support member may also comprise a flexible but non-elastic material that is configured or is adjustable to be taut around the user's limb, in order to direct forces generated by the expandable member 1902 inward, rather than outward. Although the expandable member 1902 and support member 1906 are depicted with a circular configuration, the members 1902, 1906 may have any of variety of configurations, including an oval or oblong shape, for example, which may be open like a C-shape or closed as shown.

Figure 20A:
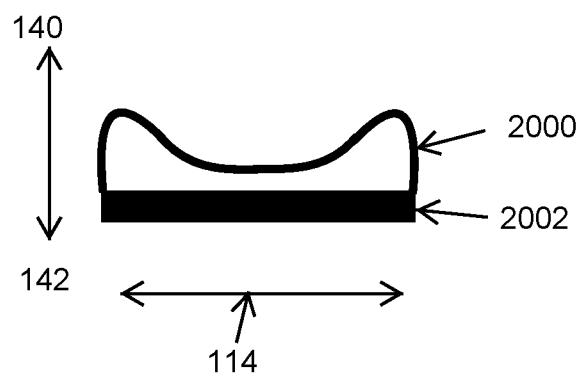
FIGS. 20A and 20B are schematic cross-sectional views of an expandable member and a frame member, in a collapsed and expanded state, respectively.
Figure 20B:
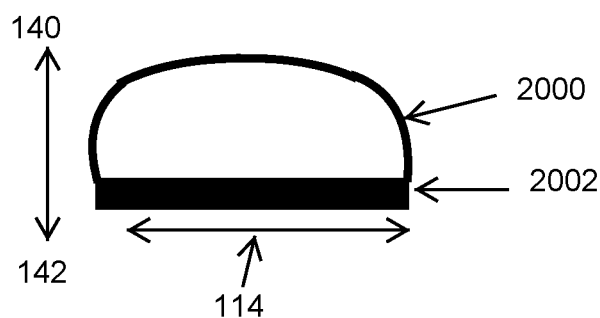
Figure 21A:
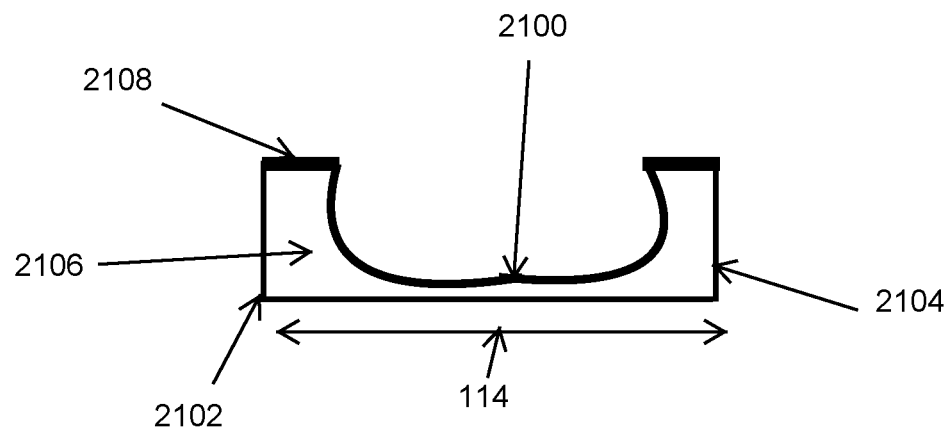
FIGS. 21A and 21B are schematic cross-sectional views of an expandable member and a frame member with side supports, in a collapsed and expanded state, respectively.
Figure 21B:
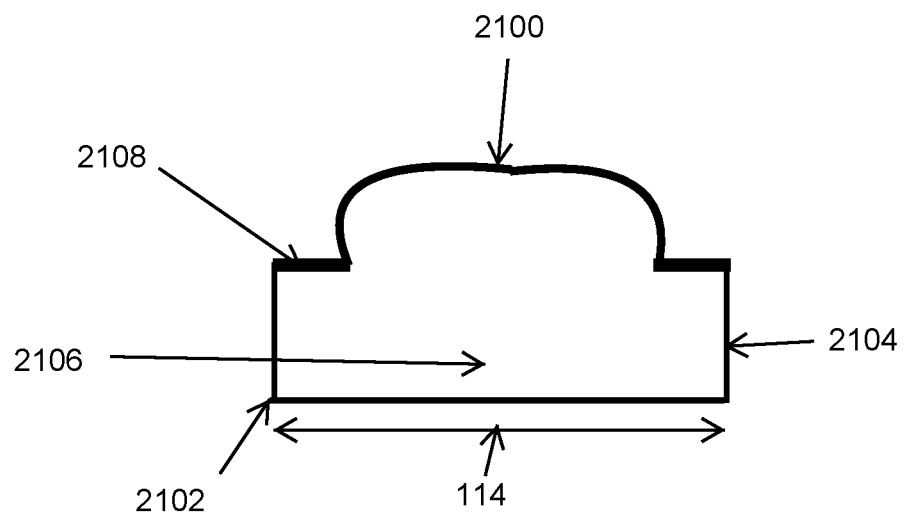

FIGS. 20A and 20B depict one example of an expandable member 2000 mounted on a support member 2002, with the expandable member in a deflated and inflated state, respectively. The support member 2002 may facilitate the application of force in the radially inward direction 140, rather than the radially outward direction 142. In other examples, as depicted in FIGS. 21A and 21B, the support member 2102 may further comprise side walls 2104 and form a cavity or recess 2106 in which the expandable member 2100 resides. In the specific example of FIGS. 21A and 21B, the expandable member 2100 may be completely within the recess 2106 when deflated, and expand beyond the tops 2108 of the side walls 2104 when fully expanded, but in other variations, the expandable member may at least partially extend out of the cavity or recess in the deflated state. Although the exemplary expandable members depicts in FIG. 20A to 21B comprises rounded or curved configurations, any of the expandable member configured described herein may be used with the support members described herein, with or without side walls.

As noted previously, the blood pressure measurement system may provide one or more alerts or message to the user relating to the user's blood pressure, and/or reminders to take blood pressure medications, and compliance with blood pressure medications. The system may also provide other information, including but not limited to summary data relating to blood pressure control and composite information showing blood pressure trends and medication compliance. Blood pressure measurements may also be used with other physiological measurements or derived values, e.g. respiratory rate, hear rate, and/or skin galvanic state, to derive other metrics such as stress level. These alerts and messages may be provided on the display located on the housing, if any, provided in the device, or may communicate with other personal electronic devices or portable multi-function devices.

Some examples of user messages include:
Report of prior day or week or month of control
Controlled blood pressure
Hypertensive status
medication regimen reminders, intake confirmation and prescription refill reminders
Prescription refills of HTN medications
Stress, wellness or fitness level The system may be located on a wearable or mobile device, while the controller may be located on the same device or a separate device, for example, a computer or a separate wearable or mobile device. In one example, the system may be located on a wrist-worn device (e.g., a watch, wrist-band, or bracelet), an article of clothing, or a smart phone or tablet. In some variations, the illumination and sensor systems may be located on the wrist-worn device, an article or clothing or a smart phone, while the controller may be located on a tablet, laptop, or desktop computer. In some variations, the system may be integrated with these other devices, but in other embodiments, the system may be in a separate module that is attachable by a user to a wearable or mobile device. For example, the system may comprise an adaptor configured to attach to a port (e.g., a USB port) of a computing device.

Although the embodiments herein have been described in relation to certain examples, various additional embodiments and alterations to the described examples are contemplated within the scope of the invention. Thus, no part of the foregoing description should be interpreted to limit the scope of the invention as set forth in the following claims. For all of the embodiments described above, the steps of the methods need not be performed sequentially. The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

The embodiments above may optionally provide the accumulation and use of data generated by the device and from other sources to enhance the content provided to users. The content may include information and materials that may be of interest to the users, as well as requests or offers. In some embodiments, accumulated information from the device or other sources may contain information that is personal to the user and in some further embodiments, may be used to assess user demographic data or identification information. Contact information, such as telephone numbers, and various electronic or postal addresses, and GPS information may be included.

In some further embodiments, the information may be helpful to the user, for example, to deliver personalized information or materials that may be of particular interest. Thus, the information may be used to control or filter, for example, the contact or materials that are provided. The information may also be used in other ways to assist the user.

The companies handling the accumulation, assessment, delivery, and other uses of the information shall be consistent with known privacy practices and policies. These practices and policies shall be applied in a consistent manner that meets or exceeds those required or otherwise established for the industry or provided by regulatory agencies, with regards to data security and privacy. In one example, data from device users may be collected for uses that are also reasonable and consistent with policies and regulations, and shall not be shared or used outside of those policies and regulations. Informed consent by the user will be obtained before such uses, and companies implement and comply with policies and regulations for safekeeping the data and restricting access to the data, and to ensure that those with access to the data also comply with data policies and regulations. In some variations, certification or assessment by third parties may be obtained to demonstrate compliance with such policies and regulations.

The embodiment further contemplate that that the users may control access or use to personal data, which may be implemented by hardware and/or software components to restrict access. In some examples where marketing materials are provided to the user, the embodiments herein may provide the user the ability to permit or block the accumulation of personal data during the set-up of the device or services relating to the device. In further examples, the device may be configured to allow the user to block GPS information relating to the delivery of marketing content, or to modify or adjust the specificity or precision of the GPS information.

While the embodiments herein relate generally to personalized data, the product features herein may also be used without the need to collect or utilize any personalized data, and without impairing the operability of the device or features. Thus, the delivery of information or content be provided in a general fashion or limited amount of identifiable user information, such as the type of device, e.g. cellphone, computer or tablet, or relating to the website or other publicly accessible sources.

What is claimed is:

1. A blood pressure measurement system, comprising:
   a device housing configured to be worn by a user and at least partially containing:
     a display screen;
     a pressure sensor; and
     an expansion actuator;
   a controller configured to control operation of the expansion actuator; and
   an expandable member coupled to the device housing and configured to at least partially engage a circumference of a limb, thereby securing the device housing to the user, the expandable member having a plurality of expandable cells comprising:
     a first set of expandable cells each having an inner surface facing the limb of the user, and an outer surface opposite the inner surface;
     a second set of expandable cells stacked with the first set of expandable cells and at least partially extending around the outer surface of the first set of expandable cells; wherein:
     operation of the expansion actuator controls a pressure within at least one of the first or second sets of expandable cells;
     the pressure sensor is configured to output a signal indicative of a blood pressure of the user; and
     the display screen is configured to display a visual output associated with the blood pressure of the user.

2. The system of claim 1, wherein the expandable member is configured to apply an increased pressure to the limb of the user in response to the expansion actuator increasing the pressure within the at least one of the first or second expandable cells.

3. The system of claim 2, wherein the expansion actuator comprises an air pump.

4. The system of claim 1, wherein:
   the expandable member comprises a first length, a width and a vertical dimension, wherein:
     the first length is orthogonal to the width and the vertical dimension;
     the width is orthogonal to the vertical dimension;
     the first length is greater than or equal to the width; and
     the width is greater than or equal to the vertical dimension; and
   the plurality of expandable cells each comprise a second length, wherein:
     the second lengths of the plurality of expandable cells are aligned to each other.

5. The system of claim 4, wherein the second lengths of the plurality of expandable cells are aligned with the first length of the expandable member.

6. The system of claim 4, where the second lengths of the plurality of expandable cells are aligned with the width of the expandable member.

7. The system of claim 4, wherein each of the plurality of expandable cells comprises an elongated cylindrical shape.

8. The system of claim 4, wherein each of the plurality of expandable cells comprises an elongated oblong shape.

9. The system of claim 4, wherein:
   the plurality of expandable cells is a first plurality of expandable cells;
   the expandable member further comprises a second plurality of expandable cells;
   the first plurality of expandable cells comprises lengths that are aligned with the first length of the expandable member; and
   the second plurality of expandable cells comprise lengths that are aligned with the width of the expandable member.

10. The system of claim 1, wherein the at least one of the plurality of expandable cells comprises an expandable sensing cell located on a skin contact surface of the expandable member.

11. The system of claim 1, wherein a lateral surface of each of the plurality of expandable cells is folded outward in a collapsed state.

12. The system of claim 1, wherein:
   the first set of expandable cells comprise a first cell and a second cell;
   the first cell is positioned adjacent to the second cell; and
   the expandable member comprises a wall segment that defines a first portion of the first cell and a second portion of the second cell.

13. The system of claim 1, wherein each cell in the first set of expandable cells each comprise a polygonal structure having at least three sides.

14. A wearable device for measuring blood pressure, comprising:
   a housing;
   a display at least partially within the housing;
   a controller;
   a wristband configured to at least partially encircle a limb of a user, thereby coupling the housing to the user, and having multiple inflatable cells that encircle the limb, the multiple inflatable cells comprising:
     a first set of inflatable cells having an inner surface facing the limb of the user, and an outer surface opposite the inner surface;
     a second inflatable cell stacked with the first set of inflatable cells and at least partially extending around the outer surface of the first set of inflatable cells;
   an air pump operably connected to at least one inflatable cell of the multiple inflatable cells, the air pump configured to increase a pressure within the at least one inflatable cell at least partially in response to receiving a first signal from the controller;
   a valve coupled to the at least one inflatable cell and configured to release air from the at least one inflatable cell at least partially in response to receiving a second signal from the controller; and
   a pressure sensor configured to measure the pressure within the at least one inflatable cell and output a third signal to the controller indicative of the pressure within the at least one inflatable cell;
   wherein the wearable device is configured to estimate a blood pressure of the user at least partially in response to at least one of the first signal, the second signal, or the third signal.

15. The wearable device of claim 14, further comprising a sound sensor configured to output a fourth signal to the controller at least partially in response to detecting one or more sounds associated with the blood pressure of the user.

16. The wearable device of claim 14, wherein a volume of each of the multiple inflatable cells each extends around at least a portion of a circumference of the limb.

17. The wearable device of claim 14, wherein a volume of each of the multiple inflatable cells extends transverse to a circumference of the limb.

18. The wearable device of claim 14, wherein:
each of the multiple inflatable cells further comprises an opening; and
the openings in the multiple inflatable cells collectively connect volumes of the multiple inflatable cells.

19. A blood pressure measurement device, comprising:
a band configured to be worn around a limb of a user, the band comprising multiple expandable cells coupled together to engage a circumference of the limb, wherein the multiple expandable cells comprise:
a first set of expandable cells having an inner surface facing the limb of the user, and an outer surface opposite the inner surface;
a second set of expandable cells stacked with the first set of expandable cells and at least partially extending around the outer surface of the first set of expandable cells;
a pressure sensor coupled with at least one of the multiple expandable cells, the pressure sensor configured to detect a fluid pressure within the at least one of the multiple expandable cells and output a first signal indicative of the fluid pressure; and
a housing coupled to the band and containing a controller configured to receive the first signal and estimate a blood pressure of the user; and
a display at least partially contained by the housing and configured to display a visual output indicative of the blood pressure of the user.

20. The blood pressure measurement device of claim 19, wherein:
each cell of the multiple expandable cells comprises a same shape; and
the band is defined by a repeating pattern of the multiple expandable cells.

* * * * *